(12) United States Patent
Ren et al.

(10) Patent No.: US 9,745,319 B2
(45) Date of Patent: Aug. 29, 2017

(54) IRREVERSIBLE COVALENT INHIBITORS OF THE GTPASE K-RAS G12C

(71) Applicant: Araxes Pharma LLC, La Jolla, CA (US)

(72) Inventors: Pingda Ren, San Diego, CA (US); Yi Liu, San Diego, CA (US); Liansheng Li, San Diego, CA (US); Jun Feng, San Diego, CA (US)

(73) Assignee: ARAXES PHARMA LLC, San Diego, CA (US)

( * ) Notice: Subject to any disclaimer, the term of this patent is extended or adjusted under 35 U.S.C. 154(b) by 0 days.

(21) Appl. No.: 14/777,334

(22) PCT Filed: Mar. 14, 2014

(86) PCT No.: PCT/US2014/027454
§ 371 (c)(1),
(2) Date: Sep. 15, 2015

(87) PCT Pub. No.: WO2014/143659
PCT Pub. Date: Sep. 18, 2014

(65) Prior Publication Data
US 2016/0031898 A1    Feb. 4, 2016

Related U.S. Application Data

(60) Provisional application No. 61/852,285, filed on Mar. 15, 2013, provisional application No. 61/889,328, filed on Oct. 10, 2013.

(51) Int. Cl.
| | |
|---|---|
| *C07D 493/04* | (2006.01) |
| *A61P 35/00* | (2006.01) |
| *C07C 311/11* | (2006.01) |
| *C07C 311/17* | (2006.01) |
| *C07C 311/18* | (2006.01) |
| *A61K 31/18* | (2006.01) |
| *A61K 31/34* | (2006.01) |
| *A61K 9/00* | (2006.01) |
| *A61K 45/06* | (2006.01) |

(52) U.S. Cl.
CPC .......... *C07D 493/04* (2013.01); *A61K 9/0019* (2013.01); *A61K 9/0053* (2013.01); *A61K 31/18* (2013.01); *A61K 31/34* (2013.01); *A61K 45/06* (2013.01); *C07C 311/11* (2013.01); *C07C 311/17* (2013.01); *C07C 311/18* (2013.01)

(58) Field of Classification Search
CPC ............................ C07D 493/04; A61K 31/34
USPC .................. 514/469, 470; 549/464
See application file for complete search history.

(56) References Cited

U.S. PATENT DOCUMENTS

| | | |
|---|---|---|
| 3,752,660 A | 8/1973 | Little |
| 4,649,219 A | 3/1987 | Itoh et al. |
| 5,033,252 A | 7/1991 | Carter |
| 5,052,558 A | 10/1991 | Carter |
| 5,323,907 A | 6/1994 | Kalvelage |
| 5,731,352 A | 3/1998 | Lesieur et al. |
| 5,861,510 A | 1/1999 | Piscopio et al. |
| 5,863,949 A | 1/1999 | Robinson et al. |
| 6,214,872 B1 | 4/2001 | Robinson |
| 6,903,118 B1 | 6/2005 | Biedermann et al. |
| 7,595,397 B2 | 9/2009 | Zindell et al. |
| 8,399,454 B2 | 3/2013 | Bian et al. |
| 8,426,401 B2 | 4/2013 | Bian et al. |
| 8,604,017 B2 | 12/2013 | Bian et al. |
| 8,697,684 B2 | 4/2014 | Bian et al. |
| 8,741,887 B2 | 6/2014 | Bian et al. |
| 9,227,978 B2 | 1/2016 | Ren et al. |
| 2002/0169300 A1 | 11/2002 | Waterman et al. |
| 2003/0022344 A1 | 1/2003 | Williams et al. |
| 2003/0166620 A1 | 9/2003 | Lee et al. |
| 2005/0012070 A1 | 1/2005 | Inoue et al. |
| 2005/0227997 A1 | 10/2005 | Noe et al. |
| 2008/0004348 A1 | 1/2008 | Yous et al. |
| 2009/0054402 A1 | 2/2009 | Wang et al. |
| 2010/0331300 A1 | 12/2010 | Bian et al. |
| 2011/0230476 A1 | 9/2011 | Niu et al. |
| 2011/0269244 A1 | 11/2011 | Petter et al. |
| 2011/0311447 A1 | 12/2011 | Tu et al. |
| 2013/0029964 A1 | 1/2013 | Aoki et al. |
| 2013/0302407 A1 | 11/2013 | Rao et al. |
| 2014/0288045 A1 | 9/2014 | Ren et al. |
| 2015/0087628 A1 | 3/2015 | Ostrem et al. |
| 2015/0239900 A1 | 8/2015 | Li et al. |
| 2016/0108019 A1 | 4/2016 | Li et al. |
| 2016/0159738 A1 | 6/2016 | Ren et al. |
| 2016/0166571 A1 | 6/2016 | Janes et al. |
| 2016/0368930 A1 | 12/2016 | Ostrem et al. |
| 2017/0022184 A1 | 1/2017 | Li et al. |

FOREIGN PATENT DOCUMENTS

| | | |
|---|---|---|
| CN | 1267291 A | 9/2000 |
| EP | 0 606 046 A1 | 7/1994 |
| EP | 0 780 386 A1 | 6/1997 |
| EP | 0 818 442 A2 | 1/1998 |
| EP | 0 931 788 A2 | 7/1999 |

(Continued)

OTHER PUBLICATIONS

Appel et al., "Supramolecular Cross-Linked Networks via Host-Guest Complexation with Cucurbit[8]uril," *J. Am. Chem. Soc.* 132(40):14251-14260, Jul. 2010.
Barbe et al., "Highly Chemoselective Metal-Free Reduction of Tertiary Amides," *J. Am. Chem. Soc.* 130:18-19, 2008.

(Continued)

*Primary Examiner* — Irina Neagu
(74) *Attorney, Agent, or Firm* — Seed IP Law Group LLP

(57) ABSTRACT

Irreversible inhibitors of K-Ras, H-Ras or N-ras protein comprising a G12C mutation are provided. Also disclosed are methods to regulate the activity of K-Ras, H-Ras or N-ras protein comprising G12C mutation and methods to disease mediated by K-Ras, H-Ras or N-ras G12C.

11 Claims, 2 Drawing Sheets

(56) References Cited

FOREIGN PATENT DOCUMENTS

| | | |
|---|---|---|
| EP | 1 004 578 A1 | 5/2000 |
| GB | 939516 A | 10/1963 |
| JP | 59-163372 A | 9/1984 |
| JP | 2005-502623 A | 1/2005 |
| JP | 2007-16011 A | 1/2007 |
| JP | 2008-524154 A | 7/2008 |
| WO | 90/05719 A1 | 5/1990 |
| WO | 96/13262 A1 | 5/1996 |
| WO | 96/27583 A1 | 9/1996 |
| WO | 96/33172 A1 | 10/1996 |
| WO | 98/03516 A1 | 1/1998 |
| WO | 98/07697 A1 | 2/1998 |
| WO | 98/30566 A1 | 7/1998 |
| WO | 98/33496 A1 | 8/1998 |
| WO | 98/33768 A1 | 8/1998 |
| WO | 98/34915 A1 | 8/1998 |
| WO | 98/34918 A1 | 8/1998 |
| WO | 98/57948 A1 | 12/1998 |
| WO | 99/29667 A1 | 6/1999 |
| WO | 99/52889 A1 | 10/1999 |
| WO | 99/52910 A1 | 10/1999 |
| WO | 03/004480 A2 | 1/2003 |
| WO | 2004/074283 A1 | 9/2004 |
| WO | 2005/070891 A2 | 8/2005 |
| WO | 2005/082892 A1 | 9/2005 |
| WO | 2006/066948 A1 | 6/2006 |
| WO | 2007/113226 A1 | 10/2007 |
| WO | 2007/144394 A2 | 12/2007 |
| WO | 2008/009078 A2 | 1/2008 |
| WO | 2010/027746 A2 | 3/2010 |
| WO | 2010/087399 A1 | 8/2010 |
| WO | 2010/121918 A1 | 10/2010 |
| WO | 2011/031896 A2 | 3/2011 |
| WO | 2011/093524 A1 | 8/2011 |
| WO | 2011/148922 A1 | 12/2011 |
| WO | 2011/153553 A2 | 12/2011 |
| WO | 2012/016082 A1 | 2/2012 |
| WO | 2012/054716 A1 | 4/2012 |
| WO | 2013/064068 A1 | 5/2013 |
| WO | 2013/155223 A1 | 10/2013 |
| WO | 2014/143659 A1 | 9/2014 |
| WO | 2014/152588 A1 | 9/2014 |
| WO | 2014/159837 A1 | 10/2014 |
| WO | 2015/054572 A1 | 4/2015 |
| WO | 2015/144001 A1 | 10/2015 |
| WO | 2015/184349 A2 | 12/2015 |
| WO | 2016/044722 A1 | 3/2016 |
| WO | 2016/049524 A1 | 3/2016 |
| WO | 2016/164675 A1 | 10/2016 |

OTHER PUBLICATIONS

Bégué et al., "Ions a-Cetocarbenium. Influence De La Structure Sur L'Evolution Des Ions α-Cetocyclohexylcarbenium," *Tetrahedron* 31(20):2205-2511, 1975. (English Abstract Only).

Johnson et al., "The Chemistry of β-Bromopropionyl Isocyanate. I. Synthesis of 1-Aryldihydrouracils," *The Journal of Organic Chemistry* 24(9):1391-1392, Sep. 1959.

Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation," *Bioorganic & Medicinial Chemistry* 6:673-686, 1998.

Le Picard et al., "Design and Synthesis of Naphthalenic Derivatives as Potential Inhibitors of Hydroxyindole-O-methyltransferase," *Pharm. Pharmacol. Commun.* 5:183-188, 1999.

Liu et al., "*Polygonatum cyrtonema* lectin induces murine fibrosarcoma L929 cell apoptosis and autophagy via blocking Ras-Raf and PI3K-Akt signaling pathways," *Biochimie* 92:1934-1938, 2010.

Loboda et al., "A gene expression signature of RAS pathway dependence predicts response to PI3K and RAS pathway inhibitors and expands the population of RAS pathway activated tumors," *BMC Medical Genomics* 3(26): 1-11, 2010.

Palmioli et al., "Selective cytotoxicity of a bicyclic Ras inhibitor in cancer cells expressing K-Ras$^{G13D}$," *Biochemical and Biophysical Research Communications* 386(4):593-597, Sep. 2009.

Pédeboscq et al., "Synthesis and evaluation of apoptosis induction of thienopyrimidine compounds on KRAS and BRAF mutated colorectal cancer cell lines," *Bioorganic & Medicinal Chemistry* 20:6724-6731, 2012.

Peri et al., "Arabinose-derived bicyclic amino acids: synthesis, conformational analysis and construction of an $α_v β_3$-selective RGD peptide," *J. Am. Chem. Soc., Perkins Trans* 1(5):638-644, Feb. 2002.

Peri et al., "Sugar-Derived Ras Inhibitors: Group Epitope Mapping by NMR Spectroscopy and Biological Evaluation," *Eur. J. Org. Chem.* 2006(16):3707-3720, Aug. 2006.

Peri et al., "Synthesis of bicyclic sugar azido acids and their incorporation in cyclic peptides," *Chem. Commun.* 23:2303-2304, Jan. 2000.

PubChem Compound, "(2S,6R)-hexahydrofiiro[3,2-b]furan-2,6-diyl dicarbonochloridate:Compound Summary CID 53396983," Oct. 30, 2011, retrieved from http://pubchem.ncbi.nlm.nih.gov/compound/53396983, 6 pages.

PubChem Compound, "(4-hydroxypiperidin-1-yl)-pyridin-4-ylmethanone: AC1L5BNJ," retrieved on Feb. 17, 2014, from http://pubchem.ncbi.nlm.nih.gov/summary/summary.cgi?cid=76837, Jul. 8, 2005, 5 pages.

PubChem Compound, "Compound Summary for CID 21765509: Molecular Formula $C_{18}H_{21}N_5O_8$," Dec. 5, 2007, retrieved from http://pubchem.ncbi.nlm.nih.gov/compound/21765509, 4 pages.

PubChem Compound, "Compound Summary for CID 21765511: Molecular Formula $C_{18}H_{21}N_5O_8$," Dec. 5, 2007, retrieved from http://pubchem.ncbi.nlm.nih.gov/compound/21765511, 4 pages.

PubChem Compound, "Compound Summary for CID 60018735: Molecular Formula $C_{30}H_{30}O_{13}$," Aug. 20, 2012, retrieved from http://pubchem.ncbi.nlm.nih.gov/compound/60018735#section=Top, 1 page.

PubChem Compound, "Compound Summary for CID 72623693: AGN-PC-0D83J7," Jan. 9, 2014, retrieved from http://pubchem.ncbi.nlm.nih.gov/compound/72623693, 6 pages.

PubChem Compound, "Compound Summary for CID 9897840: Molecular Formula $C_{50}H_{46}O_2$," Oct. 25, 2006, retrieved from http://pubchem.ncbi.nlm.nih.gov/compound/9897840, 6 pages.

Sasaki et al., "Selective Formation of Stable Triplexes Including a TA or a CG Interrupting Site with New Bicyclic Nucleoside Analogues (WNA)," *J. Am. Chem. Soc.* 126(2):516-528, Jan. 2004.

Streuff et al., "First asymmetric aminohydroxylation of acrylamides," *Tetrahedron: Asymmetry* 16(21):3492-3496, Oct. 2005.

Tsubaki et al., "Reduction of metastasis, cell invasion, and adhesion in mouse osteosarcoma by YM529/ONO-5920-induced blockade of the Ras/MEK/ERK and Ras/PI3K/Akt pathway," *Toxicology and Applied Pharmacology* 259(3):402-410, Jan. 2012.

Tulshian et al., "Synthesis and Phosphodiesterase Activity of Carboxylic Acid Mimetics of Cyclic Guanosine 3',5'-Monophosphate," *J. Med. Chem.* 36(9):1210-1220, Jan. 1993.

Wu et al., "Stereoselective synthesis of dioxabicycles from 1-C-allyl-2-O-benzyl-glycosides—An intramolecular cyclization between 2-O-benzyl oxygen and the allyl double bond," *Can. J. Chem.* 84(1):597-602, Jan. 2006.

Banker et al. (eds.), *Modern Pharmaceutics*, New York, Marcel Dekker, Inc., 1996, pp. 451 and 596. (3 pages).

Duncan et al., "N-Dialkylaminoalkybiphenylamines as Antimalarial and Atischistosomal Agents," *Journal of Medicinal Chemistry* 12:25-29, Jan. 1969.

Kumar et al., "Synthesis of 3-Sulfonylamino Quinolines form 1-(2-Aminophenyl) Propargyl Alcohols through a Ag(I)-Catalyzed Hydroamination, (2+3) Cycloaddition, and an Unusual Strain-Driven Ring Expansion," *Organic Letters* 17(9):2226-2229, Apr. 2015.

(56) References Cited

OTHER PUBLICATIONS

Ohnmacht, Jr. et al., "Antimalarials. 5. α-Dibutylaminomethyl- and α-(2-Piperidyl)-3-quinolinemethanols," *Journal of Medicinal Chemistry* 14(1):17-24, 1971.

Singh et al., "A Gene Expression Signature Associated with "K-Ras Addiction" Reveals Regulators of EMT and Tumor Cell Survival," *Cancer Cell* 15:489-500, Jun. 2009.

Sunaga et al., "Knockdown of Oncogenic KRAS in Non-Small Cell Lung Cancers Suppresses Tumor Growth and Sensitizes Tumor Cells to Targeted Therapy," *Molecular Cancer Therapeutics* 10(2):336-346, Feb. 2011.

Young et al., "Oncogenic and Wild-type Ras Play Divergent Roles in the Regulation of Mitogen-Activated Protein Kinase Signaling," *Cancer Discovery* 3(1):112-123, Jan. 2013.

Chemcats Chemical Abstract, Accession No. 1301347730, Sep. 9, 2015, 2 pages.

Chemocare, "Taxol," retrieved from http://www.chemocare.com/chemotherapy/drug-info/Taxol.aspx on Feb. 22, 2017, 3 pages.

Knochel et al., "Functionalization of heterocyclic compounds using polyfunctional magnesium and zinc reagents," Beilstein Journal of Organic Chemistry 7:1261-1277, 2011.

Long, "Taxol: An important compound with an impressive structure," Organic and General Chemistry at Flathead Valley Community College, Sep. 10, 2011, retrieved from https://longscience.com/2011/09/10/taxol-an-organic-compound-you-should-know-about/ on Feb. 22, 2017, 4 pages.

McMahon, "VEGF Receptor Signaling in Tumor Angiogenesis," *The Oncologist* 5(suppl. 1):3-10, 2000.

Pinedo et al., "Translational Research: The Role of VEGF in Tumor Angiogenesis," *The Oncologist* 5(suppl. 1):1-2, 2000.

Vippagunta et al., "Crystalline solids," *Advanced Drug Delivery Reviews* 48:3-26, 2001.

Arkin et al., "Binding of small molecules to an adaptive protein—protein interface," *PNAS* 100(4):1603-1608, Feb. 2003.

Choong et al., "Identification of Potent and Selective Small-Molecule Inhibitors of Caspase-3 through the Use of Extended Tethering and Structure-Based Drug Design," *J. Med. Chem.* 45:5005-5022, 2002.

Erlanson et al., "Site-directed ligand discovery," *Proc. Natl Acad. Sci. U.S.A.* 97(17):9367-9372, Aug. 2000.

Forbes et al., "COSMIC 2005," *British Journal of Cancer* 94:318-322, 2006.

Gorfe et al., "Mapping the Nucleotide and Isoform-Dependent Structural and Dynamical Features of Ras Proteins," *Structure* 16:885-896, Jun. 2008.

Hall et al., "The Effect of $Mg^{2+}$ on Guanine Nucleotide Exchange Rate of $p21^{N-ras}$," *The Journal of Biological Chemistry* 261(24):10963-10965, 1986.

Hall et al., "The structural basis for the transition from Ras-GTP to Ras-GDP," *PNAS* 99(19):12138-12142, Sep. 2002.

Hardy et al., "Discovery of an allosteric in the caspases," *PNAS* 101(34):12461-12466, Aug. 2004.

Hattori et al., "Neutralizing Monoclonal Antibody Against ras Oncogene Product p21 Which Impairs Guanine Nucleotide Exchange," *Mol. Cell. Biol.* 7(5):1999-2002, May 1987.

Ito et al., "Regional Polysterism in the GTP-Bound Form of the Human c-Ha-Ras Protein," *Biochemistry* 36(30):9109-1919, Jul. 1997.

Janes et al., "Combination Therapies for Treatment of Cancer," U.S. Appl. No. 14/858,766, filed Sep. 18, 2015, 421 pages.

Jordan, "Tamoxifen: A Most Unlikely Pioneering Medicine," *Nature Reviews* 2:205-213, Mar. 2003.

Kraulis et al., "Solution Structure and Dynamics of Ras p21-GDP Determined by Heteronuclear Three- and Four-Dimensional NMR Spectroscopy," *Biochemistry* 33:3515-3531, 1994.

Lee et al., "The mutation spectrum revealed by paired genome sequences from a lung cancer patient," *Nature* 465:473-477, May 2010.

Lenzen et al., "[10] Analysis of Intrinsic and CDC25-Stimulated Guanine Nucleotide Exchange of $p21^{ras}$—Nucleotide Complexes by Fluorescence Measurements," *Methods in Enzymology* 255:95-109, 1995.

Li et al., "Substituted Quinazoline Compounds and Methods of Use Thereof," U.S. Appl. No. 15/093,951, filed Apr. 8, 2016, 349 pages.

Li et al., "Substituted Quinazoline Compounds and Methods of Use Thereof," U.S. Appl. No. 15/217,304, filed Jul. 22, 2016, 131 pages.

Malani et al., "Synthesis, characterization and in vitro screening on bacterial, fungal and malarial strain of piprazinyl cyano biphenyl based compounds," *Bioorganic Chemistry* 51:16-23, 2013.

Margarit et al., "Structural Evidence for Feedback Activation by Ras•GTP of the Ras-Specific Nucleotide Exchange Factor SOS," *Cell* 112:685-695, Mar. 2008.

Milburn et al., "Molecular Switch for Signal Transduction: Structural Differences Between Active and Inactive Forms of Protooncogenic ras Proteins," *Science* 247(4945):939-945, Feb. 1990.

Ostrem et al., "K-Ras(G12C) inhibitors allosterically control GTP affinity and effector interactions," *Nature* 503(7477):548-551, Nov. 2013.

Pacold et al., "Crystal Structure and Functional Analysis of Ras Binding to Its Effector Phosphoinositide 3-Kinase γ," *Cell* 103(6):931-943, Dec. 2000.

Palmioli et al., "First experimental identification of Ras-inhibitor binding interface using a water-soluble Ras ligand," *Bioorganic and Medicinal Chemistry* 19:4217-4222, 2009.

PubChem Compound, "AKOS024742141," Nov. 27, 2010, retrieved from http://pubchem.ncbi.nim.nih.gov/compound/49702158#x304, CID 49702158, 12 pages.

PubChem Compound, "SCHEMBL6674271," Dec. 1, 2012, retrieved from http://pubchem.ncbi.nim.nih.gov/compound/69861127#x304, CID 69861127, 12 pages.

Ren et al., "Covalent Inhibitors of KRAS G12C," U.S. Appl. No. 14/933,734, filed Nov. 5, 2015, 355 pages.

Rensland et al., "Substrate and Product Structural Requirements for Binding of Nucleotides to H-ras p21: The Mechanism of Discrimination between Guanosine and Adenosine Nucleotides," *Biochemistry* 34(2):593-599, 1995.

Spiegel et al., "Small-molecule modulation of Ras signaling," *Nature Chemical Biology* 10:613-622, Aug. 2014.

Sydor et al., "Transient Kinetic Studies on the Interaction of Ras and the Ras-Binding Domain of c-Raf-1 Reveal Rapid Equilibration of the Complex," *Biochemistry* 37:14292-14299, 1998.

Taveras et al., "Ras Oncoprotein Inhibitors: The Discovery of Potent, Ras Nucleotide Exchange Inhibitors and the Structural Determination of a Drug-Protein Complex," *Bioorganic and Medicinal Chemistry* 5(1):125-133, 1997.

Vetter et al., "The Guanine Nucleotide-Binding Switch in Three Dimensions," *Science* 294(5545):1299-1304, Nov. 2001.

Wolff, (ed.), *Burger's Medicinal Chemistry and Drug Discovery, Fifth Edition, vol. 1: Principles and Practice*, San Diego, California, John Wiley & Sons, 1994, pp. 975-977. (4 pages).

Yang et al., "Fragment-Based Discovery of Nonpeptidic BACE-1 Inhibitors Using Tethering," *Biochemistry* 48:4488-4496, 2009.

Zenkl et al., "Sugar-Responsive Fluorescent Nanospheres," *Macromol. Biosci.* 8:146-152, 2008.

| Status | Oncogene | Tumor Type | Cumulative Mutation Frequency (All Tumors) |
|---|---|---|---|
| Approved | Bcr-Abl | 90% CML | <1% |
| | EGFR | 10% NSCLC | <5% |
| | ALK | 5% NSCLC | <1% |
| | B-Raf | 66% Melanoma | <5% |
| In Developement | Flt3 | 25% AML | <1% |
| | PI3kα | 25% Breast; 25% Endometrial; 15% CRC | 15-20% |
| Undruggable | K-Ras | >80% Pancreatic; >40% colon >20% lung | ~20% |

*FIG. 1*

IRREVERSIBLE COVALENT INHIBITORS OF THE GTPASE K-RAS G12C

BACKGROUND OF THE INVENTION

Ras represents a group of closely related monomeric globular protein of 189 amino acids (21 kDa molecular mass) which is associated with the plasma membrane and which binds either GDP or GTP. Ras acts as a molecular switch. When Ras contains bound GDP it is in the resting or off position and is "inactive". In response to exposure of the cell to certain growth promoting stimuli, Ras is induced to exchange its bound GDP for a GTP. With GTP bound, Ras is "switched on" and is able to interact with and activate other proteins (its "downstream targets"). The Ras protein itself has a very low intrinsic ability to hydrolyze GTP back to GDP, thus turning itself into the off state. Switching Ras off requires extrinsic proteins termed GTPase-activating proteins (GAPs) that interact with Ras and greatly accelerate the conversion of GTP to GDP. Any mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive Ras signaling may ultimately lead to cancer.

Structurally, Ras proteins contain a G domain which is responsible for the enzymatic activity of Ras—the guanine nucleotide binding and the hydrolysis (GTPase reaction). It also contains a C-terminal extension, known as the CAAX box, which may be post-translationally modified and is responsible for targeting the protein to the membrane. The G domain is approximately 21-25 kDa in size and it contains a phosphate binding loop (P-loop). The P-loop represents the pocket where the nucleotides are bound in the protein, and this is the rigid part of the domain with conserved amino acid residues which are essential for nucleotide binding and hydrolysis (Glycine 12, Threonine 26 and Lysine 16). The G domain also contains the so called Switch I (residues 30-40) and Switch II (residues 60-76) regions, both of which are the dynamic parts of the protein which are often represented as the "spring-loaded" mechanism because of their ability to switch between the resting and loaded state. The key interaction is the hydrogen bonds formed by Threonine-35 and glycine-60 with the γ-phosphate of GTP which maintain Switch 1 and Switch 2 regions respectively in their active conformation. After hydrolysis of GTP and release of phosphate, these two relax into the inactive GDP conformation.

The most notable members of the Ras subfamily are HRAS, KRAS and NRAS, mainly for being implicated in many types of cancer. However, there are many other members including DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; RRAS2.

Mutations in any one of the three main isoforms of RAS (H-Ras, N-Ras, or K-Ras) genes are among the most common events in human tumorigenesis. About 30% of all human tumors are found to carry some mutation in Ras genes. Remarkably, K-Ras mutations are detected in 25-30% of tumors (FIG. 1). By comparison, the rates of oncogenic mutation occurring in the N-Ras and H-Ras family members are much lower (8% and 3% respectively). The most common K-Ras mutations are found at residue G12 and G13 in the P-loop and at residue Q61.

G12C is a frequent mutation of K-Ras gene (glycine-12 to cysteine). This mutation had been found in about 13% of cancer occurrences, about 43% of lung cancer occurrences, and in almost 100% of MYH-associates polyposis (familial colon cancer syndrome). However targeting this gene with small molecules is a challenge.

INCORPORATION BY REFERENCE

All publications and patent applications mentioned in this specification are herein incorporated by reference to the same extent as if each individual publication or patent application was specifically and individually indicated to be incorporated by reference.

SUMMARY OF THE INVENTION

In one aspect, the disclosure provides a compound of Formula I:

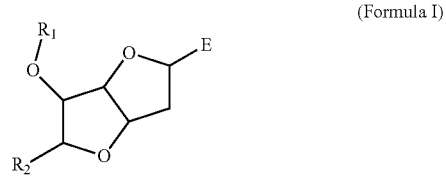

(Formula I)

In one embodiment, $R_1$ is alkyl, heteroalkyl, cycloalkyl, cycloheteroalkyl, aryl, or heteroaryl moiety each of which is either unsubstituted or substituted with one or more $R_3$ groups; $R_2$ is hydrogen, halogen, alkoxy, alkyl, heteroalkyl, cycloalkyl, cycloheteroalkyl, aryl or heteroaryl moiety each of which is either unsubstituted or substituted with one or more $R_4$ groups; $R_3$ is hydrogen, halogen, $OR_5$, $NR_6R_7$, cyano, oxo, alkyl, heteroalkyl, cycloalkyl, cycloheteroalkyl, aryl or heteroaryl moiety, each of which is either unsubstituted or substituted with one or more $R_8$ groups; $R_5$, $R_6$ and $R_7$ are independently hydrogen, alkyl, heteroalkyl, cycloalkyl, cycloheteroalkyl, aryl or heteroaryl moiety each of which is either unsubstituted or substituted with one or more $R_9$ groups; $R_4$, $R_8$ and $R_9$ are independently hydrogen, halogen, hydroxy, alkyl, alkoxy, heteroalkyl, cycloalkyl, cycloheteroalkyl, aryl, or heteroaryl moiety each of which is either unsubstituted or substituted with one or more $R_{10}$ groups; each $R_{10}$ is independently hydrogen, halogen, hydroxy, alkyl, heteroalkyl, cycloalkyl, cycloheteroalkyl, aryl, or heteroaryl moiety; and E is an electrophile capable of forming a covalent bond with the cysteine residue at position 12 of a K-Ras G12C mutant protein.

In some embodiments, $R_2$ is —$CH_2$—$R_7$. In some embodiments, $R_7$ is OH. In some embodiments, $R_7$ is —O—$CH_2$—$R_{13}$, where $R_{13}$ may optionally be $C_6H_5$. In some embodiments, $R_1$ is a alkyl, unsubstituted or substituted with one or more $R_3$ groups. In some embodiments, $R_1$ is a alkyl substituted with one or more $R_3$ groups and wherein $R_3$ is aryl. In some embodiments, $R_1$ is —$CH_2$—$C_6H_5$. In some embodiments, E is selected from the group consisting of:

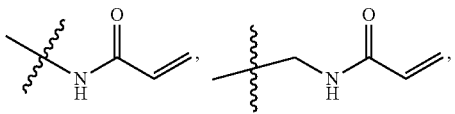

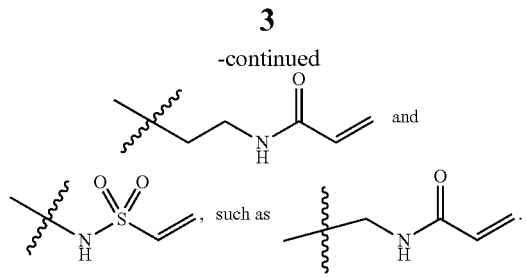

In some embodiments, the compound is selected from the group of compounds shown in Table 1.

In one aspect, the disclosure provides a compound of Formula II:

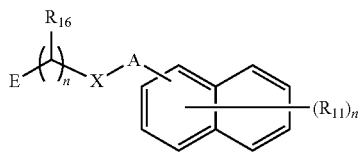

(Formula II)

In one embodiment, each $R_{11}$ is halogen, $OR_{12}$, $NR_{13}R_{14}$, alkyl, heteroalkyl, cycloalkyl, cycloheteroalkyl, aryl or heteroaryl moiety, each of which is either unsubstituted or substituted with one or more $R_{15}$ groups; n is an integer between 0-6; each $R_{12}$, $R_{13}$, $R_{14}$, and $R_{15}$ is independently hydrogen, halogen, hydroxy, alkyl, alkoxy, heteroalkyl, cycloalkyl, cycloheteroalkyl, aryl or heteroaryl moiety; X is bond, $CHR_{17}$, $NR_{17}$, CO, or $SO_2$; A is a bond, O, $NR_{18}$, S, $CR_{18}R_{19}$, CO, SO or $SO_2$; $R_{16}$ is hydrogen, unsubstituted alkyl, alkyl substituted with one or more $R_{20}$ groups, or heterocycloalkyl; in each occurrence $R_{17}$, $R_{18}$, $R_{19}$ and $R_{20}$ are independently hydrogen, halogen, hydroxyl, alkyl, cycloalkyl, heteroalkyl, heterocycloalkyl, aryl or heteroaryl; and E is an electrophile capable of forming a covalent bond with the cysteine residue at position 12 of a K-Ras (or H-Ras or N-Ras) G12C mutant protein.

In some embodiments, the compound has a Formula IIa:

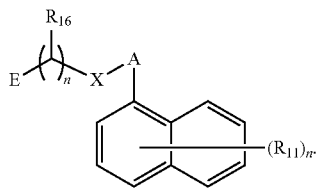

(Formula IIa)

In some embodiments, the compound has a Formula IIb:

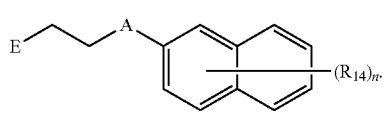

(Formula IIb)

In some embodiments, n is 0. In some embodiments, E is selected from the group consisting of:

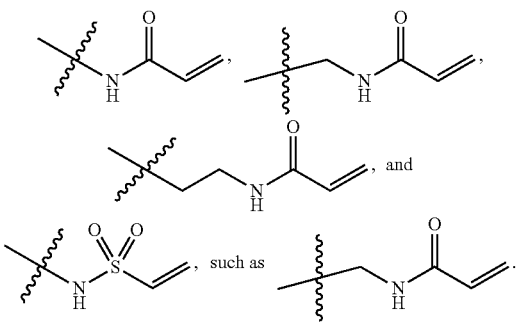

In some embodiments, A is O. In some embodiments, A is NH. In some embodiments, the compound is selected from the group of compounds shown in Table 2.

In one aspect, the disclosure provides a pharmaceutical composition comprising a pharmaceutically acceptable carrier and a compound in accordance with an embodiment of the present invention. In some embodiments, the pharmaceutical composition is suitable for oral administration. In some embodiments, the pharmaceutical composition is suitable for injection.

In one aspect, the disclosure provides a method for regulating activity of K-Ras, H-Ras or N-ras G12C mutant protein. In one embodiment, the method comprises reacting the K-Ras, H-Ras or N-ras G12C mutant protein with a compound in accordance with an embodiment of the present invention.

In one aspect, the disclosure provides a method of treating a disorder in a subject in need thereof. In one embodiments, the method comprises (a) determining if the subject has a K-Ras, H-Ras or N-ras G12C mutation; and (b) if the subject is determined to have the K-Ras, H-Ras or N-ras G12C mutation then administering to the subject a therapeutically effective dose of a pharmaceutical composition comprising at least one compound in accordance with an embodiment of the present invention or a salt thereof. In some embodiments, the disorder is cancer, such as pancreatic cancer, colon cancer, MYH associated polyposis, colorectal cancer, lung cancer or NSCLC.

In one aspect, the disclosure provides a method of preparing a labeled K-Ras, H-Ras or N-ras G12C mutant protein. In one embodiment, the method comprises reacting the K-Ras G12C, H-Ras or N-ras mutant protein with a compound in accordance with an embodiment of the invention, to result in the labeled K-Ras, H-Ras or N-ras G12C protein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows the common oncogenes, their tumor type and mutation frequencies.

DETAILED DESCRIPTION OF THE INVENTION

Definitions

Figure 2:
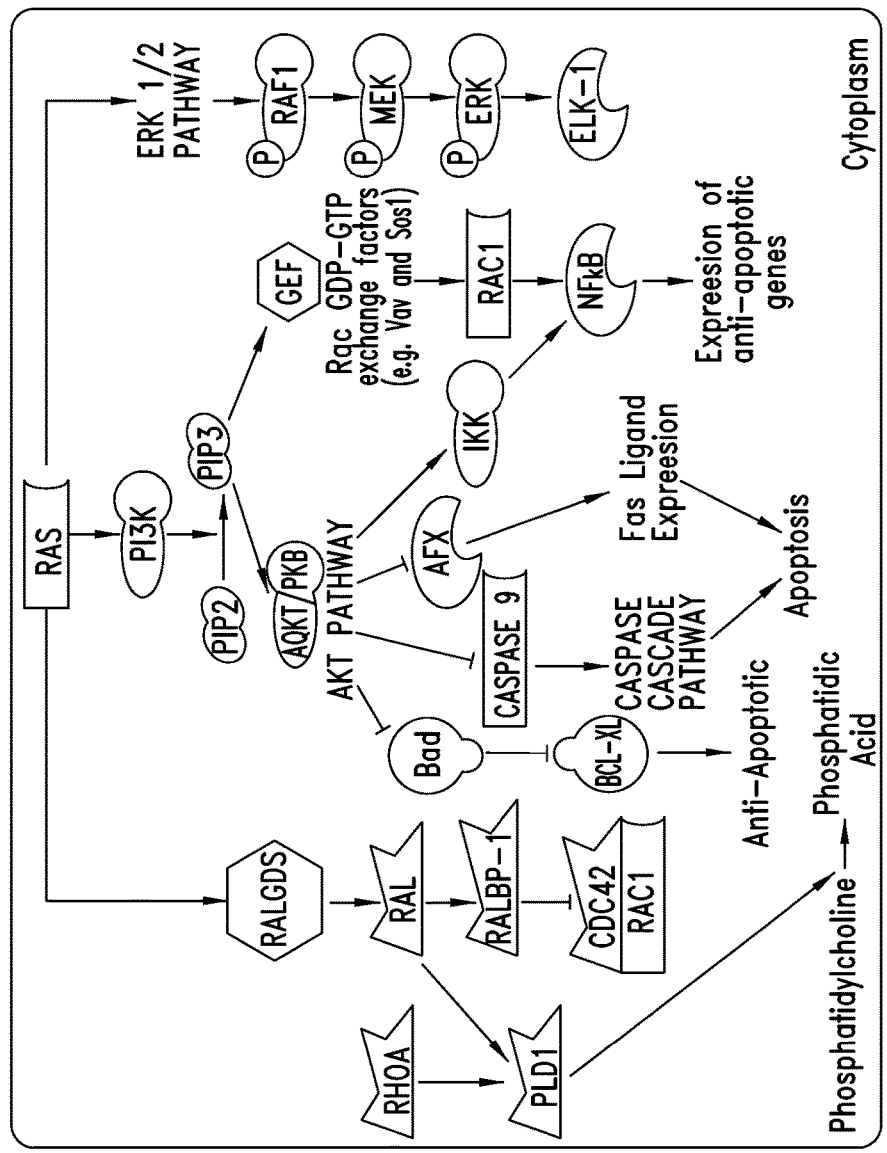
FIG. 2 shows a signal transduction pathway for Ras.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" include plural references unless the context clearly dictates otherwise.

The term "effective dose" or "therapeutically effective dose" refers to that amount of a compound described herein that is sufficient to effect the intended treatment application including but not limited to disease treatment, as defined below. The therapeutically effective amount may vary depending upon the intended application (in vivo), or the subject and disease, disorder or condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to disease disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like, when the molecule contains an acidic functionality; and when the molecule contains a basic functionality, salts of organic or inorganic acids, such as hydrochloride, hydrobromide, tartrate, mesylate (methane sulfonate), ethane sulfonate, acetate, maleate, oxalate, phosphate, and the like. In a compound with more than one basic moiety, more than one of the basic moieties may be converted to the salt form, including but not limited to a bis- or tris-salt. Alternatively, a compound having more than one basic moiety may form a salt at only one of the basic moieties.

"Subject" refers to an animal, including humans such as a mammal, for example a human. The methods described herein can be useful in both human therapeutics and veterinary applications. In some embodiments, the subject is a mammal, and in some embodiments, the subject is human.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are encompassed within the scope of the present invention.

As used herein, "alkyl" is used to mean an alkyl having carbons in a straight or branched configuration. In all embodiments of this invention, the term "alkyl" includes both branched and straight chain alkyl groups, or cyclic hydrocarbon groups, or a combination thereof. Alkyl groups are fully saturated, unsubstituted or substituted, and can include di- and multivalent radicals. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl and the like. In various embodiments an alkyl can comprise 1-12 carbons.

The term "halo" or "halogen" refers to fluoro, chloro, bromo, or iodo.

Unless otherwise specified, the term "cycloalkyl" refers to a 3-8 carbon cyclic aliphatic ring structure that is unsubstituted or substituted with, for example, alkyl, hydroxy, oxo, or halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

The term "heterocycloalkyl" refers to a substituted or unsubstituted 3-, 4-, 5-, or 6-membered saturated or partially unsaturated ring containing one, two, or three heteroatoms, preferably one or two heteroatoms independently selected from oxygen, nitrogen and sulfur; or to a bicyclic ring system containing up to 10 atoms including at least one heteroatom independently selected from oxygen, nitrogen, and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, and 5-methyl-6-chromanyl. Heterocycloalkyl may be substituted or unsubstituted. A heterocycloalkyl may also be substituted with another cycloalkyl, heterocycloalkyl, aryl or heteroaryl moiety by fusion.

The term "icycloalkyl" refers to a structure consisting of two or more cycloalkyl moieties, unsubstituted or substituted, that have one or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[3.2.1]heptyl ("norbornyl"), bicyclo [2.2.2]octyl, and the like. In various embodiments an cycloalkyl can comprise 1-12 carbons.

The term "spirocycloalkyl" or "spiro cycoalkyl" or "spiroalkyl" are cycloalkyl that have one carbon atom in common.

The term "heteroalkyl," by itself or in combination with another term, means, unless otherwise stated, a straight or branched chain, or cyclic hydrocarbon radical, or combinations thereof, consisting of at least one carbon atoms and at least one heteroatom selected from the group consisting of O, N, P, and S, and wherein the nitrogen, phosphorus, and sulfur atoms may optionally be oxidized and the nitrogen heteroatom may optionally be quaternized. The heteroatom(s) O, N, P and/or S may be placed at any interior position of the heteroalkyl group or at the position at which alkyl group is attached to the remainder of the molecule. The alkyl portion of the moiety is unsubstituted or substituted. In various embodiments an heteroalkyl can comprise 1-10 atoms (carbon plus heteroatoms).

The term "heterobicycloalkyl" refers to a bicycloalkyl structure, which is unsubstituted or substituted, in which at least one carbon atom is replaced with a heteroatom independently selected from oxygen, nitrogen, and sulfur.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl. An aryl moiety is unsubstituted or substituted.

"Heteroaryl" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). A heteroaryl moiety is unsubstituted or substituted.

The term "alkoxy" includes both branched and straight chain terminal alkyl groups attached to a linking oxygen atom. Typical alkoxy groups include methoxy, ethoxy, n-propoxy, isopropoxy, tert-butoxy and the like. An alkoxy moiety is unsubstituted or substituted.

The term "oxo" refers to an oxygen that is double bonded to a carbon atom. One in the art understands that an "oxo" requires a second bond from the atom to which the oxo is attached. Accordingly, it is understood that oxo cannot be substituted onto an aryl or heteroaryl ring, unless it forms part of the aromatic system as a tautomer.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The present invention includes all manner of rotamers and conformationally restricted states of a compound of the invention.

K-Ras G12C Inhibitors

In an aspect, the disclosure provides compounds which are capable of selectively binding to and/or modulating a G12C mutant K-Ras, H-Ras or N-ras proteins. The compounds may modulate the G12C mutant K-Ras, H-Ras or N-ras protein by reaction with an amino acid. In some embodiment the compounds of the invention selectively react with the G12C mutant K-Ras, H-Ras or N-ras proteins by forming an irreversible covalent bond with the cysteine at the 12 position. By binding to the cysteine 12 the compounds of the invention may lock the switch II of the G12C mutant K-Ras, H-Ras or N-ras into an inactive stage. This inactive stage may be distinct from those observed for GTP and GDP bound K-Ras, H-Ras or N-ras. Some compounds of the invention may also be able to perturb the switch I conformation. Because effector binding to K-Ras, H-Ras or N-ras is highly sensitive to the conformation of switch I and II, the irreversible binding of these compounds may disrupt K-Ras downstream signaling.

In some embodiments, the invention provides a compound of Formula I

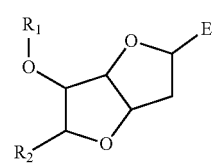

Formula I

In some embodiments, $R_1$ substituted or unsubstituted alkyl, substituted or unsubstituted heteroalkyl, substituted or unsubstituted cycloalkyl, substituted or unsubstituted cycloheteroalkyl, substituted or unsubstituted aryl, or substituted or unsubstituted heteroaryl. In some embodiments $R_1$ is substituted alkyl. In some cases $R_1$ is unsubstituted alkyl. In some embodiments $R_1$ is substituted aryl. In some cases $R_1$ is unsubstituted aryl. In some cases $R_1$ is substituted heteroalkyl. In some cases $R_1$ is unsubstituted heteroalkyl. In some cases $R_1$ is substituted heteroaryl. In some cases $R_1$ is unsubstituted heteroaryl. In some embodiments $R_1$ an alkyl group substituted with one or more $R_3$ groups. In some embodiments $R_1$ a heteroalkyl group substituted with one or more $R_3$ groups. In some embodiments $R_1$ an aryl group substituted with one or more $R_3$ groups. In some embodiments $R_1$ a heteroaryl group substituted with one or more $R_3$ groups. In some embodiments $R_1$ is a substituted or unsubstituted benzyl group. In some embodiments $R_1$ is a substituted benzyl group. In some embodiments $R_1$ is an unsubstituted benzyl group.

In some embodiments, $R_1$ may be capable of reversible interaction with K-Ras, H-Ras or N-ras G12C mutant protein. In some embodiments $R_1$ may have high affinity towards K-Ras, H-Ras or N-ras and may be highly specific towards G12C K-Ras, H-Ras or N-ras. In some embodiments $R_1$ is capable of hydrophobic interaction with K-Ras, H-Ras or N-ras G12C. In some embodiments $R_1$ may be able to form hydrogen bonds with various residues of G12C K-Ras, H-Ras or N-ras protein. In some embodiments $R_1$ may interact with one or more of G10, R68, Y71, Y96 or Q99 residues in K-Ras G12C (FIG. 1). In some embodiments $R_1$ interacts with the G10 residue of K-Ras G12C. In some embodiments $R_1$ interacts with the R68 residue of K-Ras G12C. In some embodiments $R_1$ interacts with the Y71 residue of K-Ras G12C. In some embodiments $R_1$ interacts with the Y96 residue of K-Ras G12C. In some embodiments $R_1$ interacts with the Q99 residue of K-Ras G12C.

$R_2$ is hydrogen, halogen, unsubstituted or substituted alkoxy, unsubstituted or substituted alkyl, unsubstituted or substituted heteroalkyl, unsubstituted or substituted cycloalkyl, unsubstituted or substituted cycloheteroalkyl, unsubstituted or substituted aryl or unsubstituted or substituted heteroaryl moiety. In some embodiments $R_2$ is hydrogen. In some embodiments, $R_2$ is a halogen. In some embodiments $R_2$ is an alkoxy group substituted with one or more $R_4$ groups. In some embodiments $R_2$ is an unsubstituted alkoxy group. In some embodiments $R_2$ is an alkyl group substituted with one or more $R_4$ groups. In some embodiments $R_2$ is an unsubstituted alkyl group. In some embodiments $R_2$ is a heteroalkyl group substituted with one or more $R_4$ groups. In some embodiments $R_2$ is an unsubstituted heteroalkyl group. In some embodiments $R_2$ a cycloalkyl group substituted with one or more $R_4$ groups. In some embodiments $R_2$ is an unsubstituted cycloalkyl group. In some embodiments $R_2$ is a cycloheteroalkyl substituted with one or more $R_4$ groups. In some embodiments $R_2$ is a unsubstituted cycloheteroalkyl group. In some embodiments $R_2$ is an aryl substituted with one or more $R_4$ groups. In some embodiments $R_2$ is an unsubstituted aryl group. In some embodiments $R_2$ is a heteroaryl group substituted with one or more $R_4$ groups. In some embodiments $R_2$ unsubstituted a heteroaryl group. In some embodiments $R_2$ is —$CH_2$—OH. In some embodiments $R_2$ is —$CH_2$—O—$CH_2$—$C_6H_5$. $R_3$ is hydrogen, halogen, $OR_8$, $NR_9R_{10}$, cyano, substituted or unsubstituted alkyl, substituted or unsubstituted heteroalkyl, substituted or unsubstituted cycloalkyl, substituted or unsubstituted cycloheteroalkyl, substituted or unsubstituted aryl or substituted or unsubstituted heteroaryl.

In some embodiments $R_3$ is hydrogen. In some embodiments $R_3$ is oxo. In some embodiments $R_3$ is halogen. In some embodiments $R_3$ is $OR_8$. In some embodiments $R_3$ is $NR_9R_{10}$. In some embodiments $R_3$ is cyano. In some embodiments $R_3$ is unsubstituted alkyl. In some embodiments $R_3$ is an alkyl substituted with one or more $R_8$ groups. In some embodiments $R_3$ is unsubstituted heteroalkyl. In some embodiments $R_3$ is a heteroalkyl substituted with one or more $R_8$ groups. In some embodiments $R_3$ is unsubstituted cycloalkyl. In some embodiments $R_3$ is a cycloalkyl substituted with one or more $R_8$ groups. In some embodiments $R_3$ is an unsubstituted cycloheteroalkyl. In some embodiments $R_3$ is a cycloheteroalkyl substituted with one or more $R_8$ groups. In some embodiments $R_3$ is an unsubstituted aryl. In some embodiments $R_3$ is an aryl substituted with one or more $R_8$ groups. In some embodiments $R_3$ is an unsubstituted heteroaryl. In some embodiments $R_3$ is a heteroaryl substituted with one or more $R_8$ groups. In some embodiments $R_3$ is halogen. In some embodiments $R_3$ is hydroxy.

$R_5$, $R_6$ and $R_7$ are independently hydrogen, alkyl, heteroalkyl, cycloalkyl, cycloheteroalkyl, aryl or heteroaryl moiety each of which is either unsubstituted or substituted with one or more $R_9$ groups. In some embodiments $R_5$ is hydrogen. In some embodiments $R_5$ is unsubstituted alkyl. In some embodiments $R_5$ is an alkyl substituted with one or more $R_9$ groups. In some embodiments $R_5$ is unsubstituted heteroalkyl. In some embodiments $R_5$ is a heteroalkyl substituted with one or more $R_9$ groups. In some embodiments $R_5$ is unsubstituted cycloalkyl. In some embodiments $R_5$ is a cycloalkyl substituted with one or more $R_9$ groups. In some embodiments $R_5$ is unsubstituted cycloheteroalkyl. In some embodiments $R_5$ is a cycloheteroalkyl substituted with one or more $R_9$ groups. In some embodiments $R_5$ is unsubstituted aryl. In some embodiments $R_5$ is an aryl substituted with one or more $R_9$ groups. In some embodiments $R_5$ is unsubstituted heteroaryl. In some embodiments $R_5$ is a heteroaryl substituted with one or more $R_9$ groups.

In some embodiments $R_6$ is hydrogen. In some embodiments $R_6$ is unsubstituted alkyl. In some embodiments $R_6$ is an alkyl substituted with one or more $R_9$ groups. In some embodiments $R_6$ is unsubstituted heteroalkyl. In some embodiments $R_6$ is a heteroalkyl substituted with one or more $R_9$ groups. In some embodiments $R_6$ is unsubstituted cycloalkyl. In some embodiments $R_6$ is a cycloalkyl substituted with one or more $R_9$ groups. In some embodiments $R_6$ is unsubstituted cycloheteroalkyl. In some embodiments $R_6$ is a cycloheteroalkyl substituted with one or more $R_9$ groups. In some embodiments $R_6$ is unsubstituted aryl. In some embodiments $R_6$ is an aryl substituted with one or more $R_9$ groups. In some embodiments $R_6$ is unsubstituted heteroaryl. In some embodiments $R_6$ is a heteroaryl substituted with one or more $R_9$ groups.

In some embodiments $R_7$ is hydrogen. In some embodiments $R_7$ is unsubstituted alkyl. In some embodiments $R_7$ is an alkyl substituted with one or more $R_9$ groups. In some embodiments $R_7$ is unsubstituted heteroalkyl. In some embodiments $R_7$ is a heteroalkyl substituted with one or more $R_9$ groups. In some embodiments $R_7$ is unsubstituted cycloalkyl. In some embodiments $R_7$ is a cycloalkyl substituted with one or more $R_9$ groups. In some embodiments $R_7$ is unsubstituted cycloheteroalkyl. In some embodiments $R_7$ is a cycloheteroalkyl substituted with one or more $R_9$ groups. In some embodiments $R_7$ is unsubstituted aryl. In some embodiments $R_7$ is an aryl substituted with one or more $R_9$ groups. In some embodiments $R_7$ is unsubstituted heteroaryl. In some embodiments $R_7$ is a heteroaryl substituted with one or more $R_9$ groups.

$R_4$, $R_8$ and $R_9$ are independently hydrogen, oxo, cyano, halogen, hydroxy, alkyl, alkoxy, heteroalkyl, cycloalkyl, cycloheteroalkyl, aryl, or heteroaryl moiety each of which is either unsubstituted or substituted with one or more $R_{10}$ groups. In some embodiments $R_4$ is hydrogen. In some cases $R_4$ is halogen. In some cases $R_4$ is hydroxyl. In some embodiments $R_4$ is an unsubstituted alkyl. In some embodiments $R_7$ is an alkyl substituted with one or more $R_{10}$ groups. In some embodiments $R_4$ is an unsubstituted alkoxy. In some embodiments $R_7$ is an alkoxy substituted with one or more $R_{10}$ groups. In some embodiments $R_4$ is an unsubstituted heteroalkyl. In some embodiments $R_7$ is a heteroalkyl substituted with one or more $R_{10}$ groups. In some embodiments $R_4$ is an unsubstituted cycloalkyl. In some embodiments $R_4$ is a cycloalkyl substituted with one or more $R_{10}$ groups. In some embodiments $R_4$ is an unsubstituted cycloheteroalkyl. In some embodiments $R_4$ is a cycloheteroalkyl substituted with one or more $R_{10}$ groups. In some embodiments $R_4$ is an unsubstituted aryl. In some embodiments $R_4$ is an aryl substituted with one or more $R_{10}$ groups. In some embodiments $R_4$ is an unsubstituted heteroaryl. In some embodiments $R_4$ is a heteroaryl substituted with one or more $R_{10}$ groups.

In some embodiments $R_8$ is hydrogen. In some embodiments $R_8$ is cyano. In some embodiments $R_8$ is oxo. In some cases $R_8$ is halogen. In some cases $R_8$ is hydroxyl. In some embodiments $R_8$ is an unsubstituted alkyl. In some embodiments $R_8$ is an alkyl substituted with one or more $R_{10}$ groups. In some embodiments $R_8$ is an unsubstituted alkoxy. In some embodiments $R_8$ is an alkoxy substituted with one or more $R_{10}$ groups. In some embodiments $R_8$ is an unsubstituted heteroalkyl. In some embodiments $R_8$ is a heteroalkyl substituted with one or more $R_{10}$ groups. In some embodiments $R_8$ is an unsubstituted cycloalkyl. In some embodiments $R_8$ is a cycloalkyl substituted with one or more $R_{10}$ groups. In some embodiments $R_8$ is an unsubstituted cycloheteroalkyl. In some embodiments $R_8$ is a cycloheteroalkyl substituted with one or more $R_{10}$ groups. In some embodiments $R_8$ is an unsubstituted aryl. In some embodiments $R_8$ is an aryl substituted with one or more $R_{10}$ groups. In some embodiments $R_8$ is an unsubstituted heteroaryl. In some embodiments $R_8$ is a heteroaryl substituted with one or more $R_{10}$ groups.

In some embodiments $R_9$ is hydrogen. In some cases $R_9$ is halogen. In some embodiments $R_8$ is cyano. In some cases $R_9$ is hydroxyl. In some embodiments $R_9$ is an unsubstituted alkyl. In some embodiments $R_9$ is an alkyl substituted with one or more $R_{10}$ groups. In some embodiments $R_9$ is an unsubstituted alkoxy. In some embodiments $R_9$ is an alkoxy substituted with one or more $R_{10}$ groups. In some embodiments $R_9$ is an unsubstituted heteroalkyl. In some embodiments $R_9$ is a heteroalkyl substituted with one or more $R_{10}$ groups. In some embodiments $R_9$ is an unsubstituted cycloalkyl. In some embodiments $R_9$ is a cycloalkyl substituted with one or more $R_{10}$ groups. In some embodiments $R_9$ is an unsubstituted cycloheteroalkyl. In some embodiments $R_9$ is a cycloheteroalkyl substituted with one or more $R_{10}$ groups. In some embodiments $R_9$ is an unsubstituted aryl. In some embodiments $R_9$ is an aryl substituted with one or more $R_{10}$ groups. In some embodiments $R_9$ is an unsubstituted heteroaryl. In some embodiments $R_9$ is a heteroaryl substituted with one or more $R_{10}$ groups.

$R_{10}$ is independently hydrogen, halogen, hydroxy, alkyl, heteroalkyl, cycloalkyl, cycloheteroalkyl, aryl, or heteroaryl moiety. In some embodiments $R_{10}$ is hydrogen. In some embodiments $R_{10}$ is halogen. In some embodiments $R_{10}$ is hydroxyl. In some embodiments $R_{10}$ is alkyl. In some embodiments $R_{10}$ is heteroalkyl. In some embodiments $R_{10}$ is cycloalkyl. In some embodiments $R_{10}$ is cycloheteroalkyl. In some embodiments $R_{10}$ is aryl. In some embodiments $R_{10}$ is heteroaryl moiety.

In some embodiments E is an electrophile capable of bonding with a K-Ras, H-Ras or N-ras protein comprising G12C mutation. In some embodiments, the electrophile E is capable of forming an irreversible covalent bond with a G12C mutant K-Ras, H-Ras or N-ras protein. In some cases, the electrophile E may bind with the cysteine residue at the position 12 of a G12C mutant K-Ras protein. In some embodiments, E is an electrophile capable of forming a covalent bond with a residue near the Switch 2 in G12C mutant K-Ras, H-Ras or N-ras protein. In some embodiments, E is an electrophilic capable of forming a covalent bond with a residue in the Switch 2—Binding Pocket of G12C mutant K-Ras, H-Ras or N-ras protein.

E is an electrophile capable of forming a covalent bond with the cysteine residue at position 12 of a K-Ras, H-Ras or N-ras G12C mutant protein. In some cases E is selected from the group consisting of

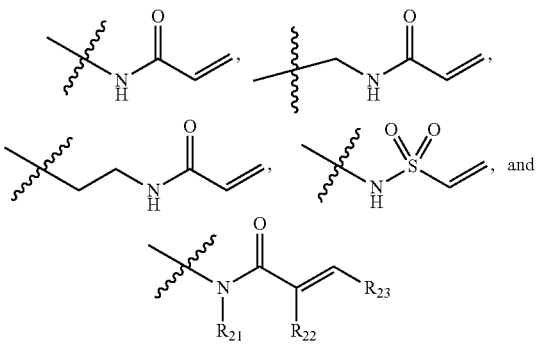

$R_{21}$ = alkyl; $R_{22}$ = CN, alkyl, $R_{23}$ = alkyl; or
$R_{22}$ and $R_{23}$ can form cyclo alkene, aryl, or cycloalkyl In some embodiments E is

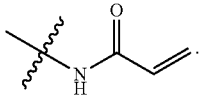

In some embodiments E is

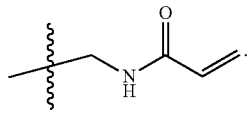 [SMILES: *CNC(=O)C=C]

In some embodiments E is

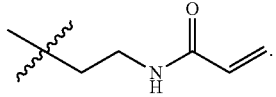 [SMILES: *CCNC(=O)C=C]

In some embodiments E is

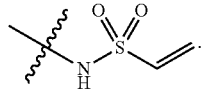 [SMILES: *NS(=O)(=O)C=C]

In other embodiments, E is

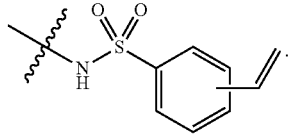

In some embodiments the invention provides compounds of Formula I as shown in Table 1.

TABLE 1

| Compound Number | Structure |
|---|---|
| I-1 | 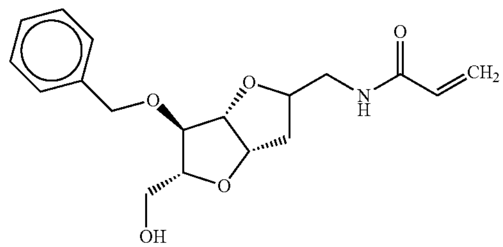 |
| I-2 | 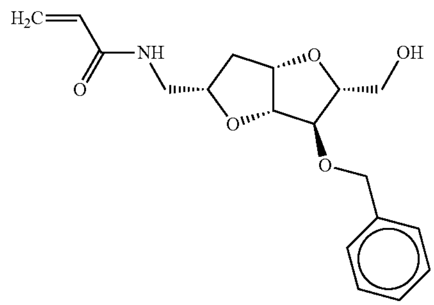 |
| I-3 | 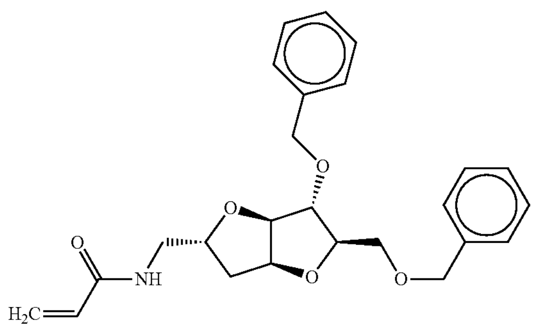 |
| I-4 | 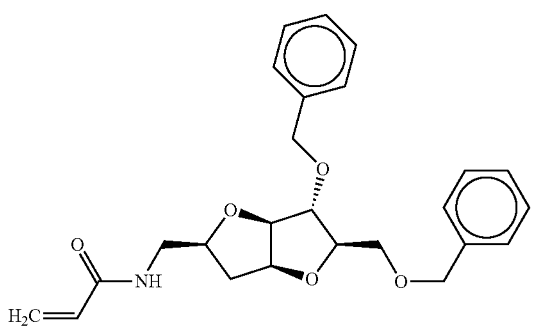 |
| I-5 | 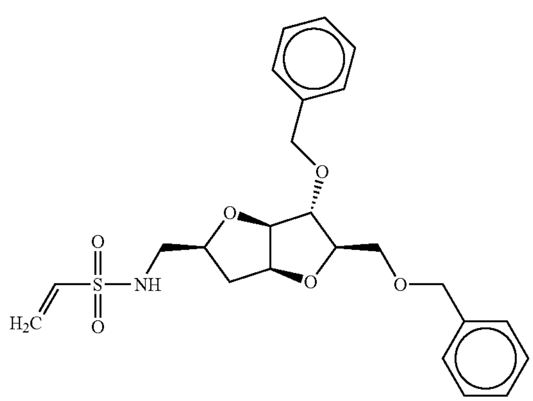 |

TABLE 1-continued

| Compound Number | Structure |
|---|---|
| I-6 | 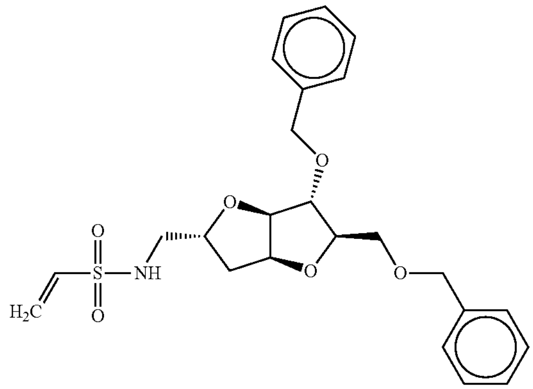 |
| I-7 | 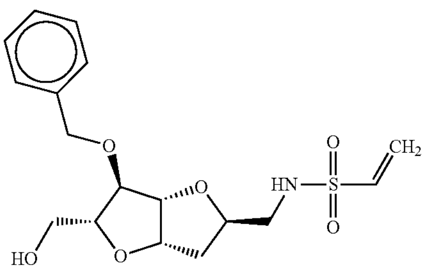 |
| I-8 | 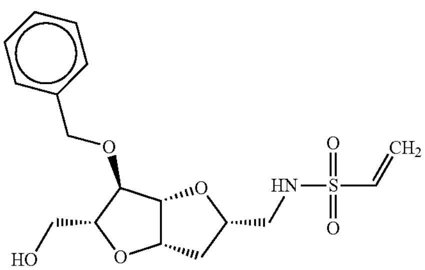 |
| I-9 | 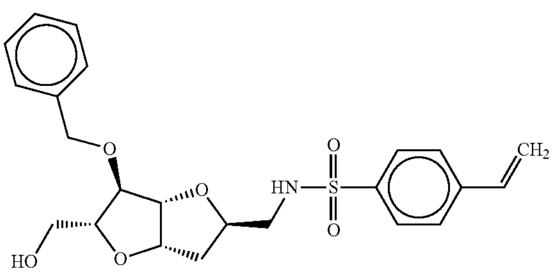 |
| I-10 | 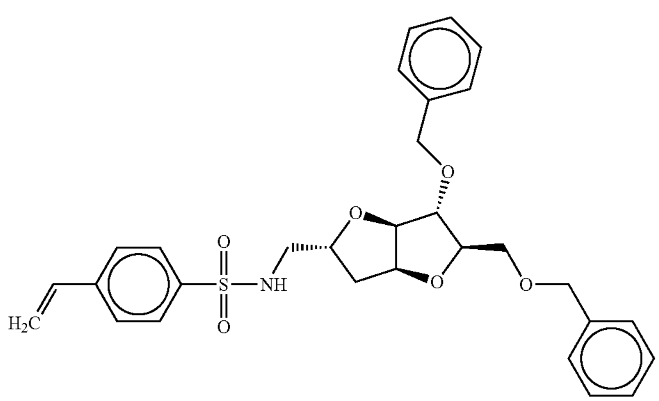 |

TABLE 1-continued

| Compound Number | Structure |
| --- | --- |
| I-11 | 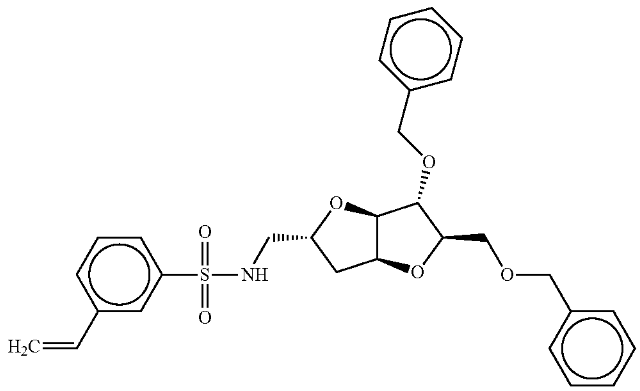 |
| I-12 | 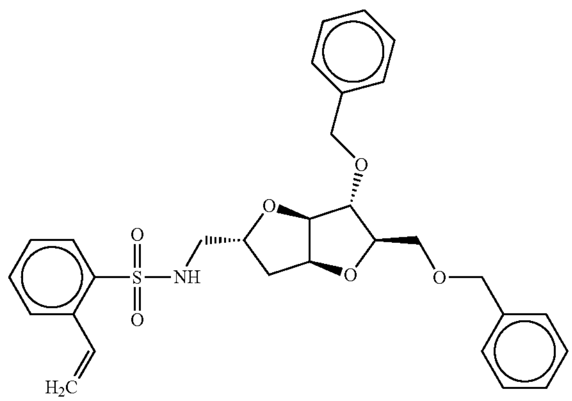 |
| I-13 | 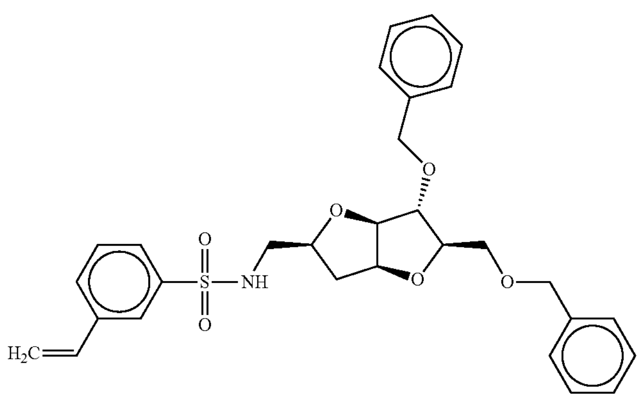 |
| I-14 | 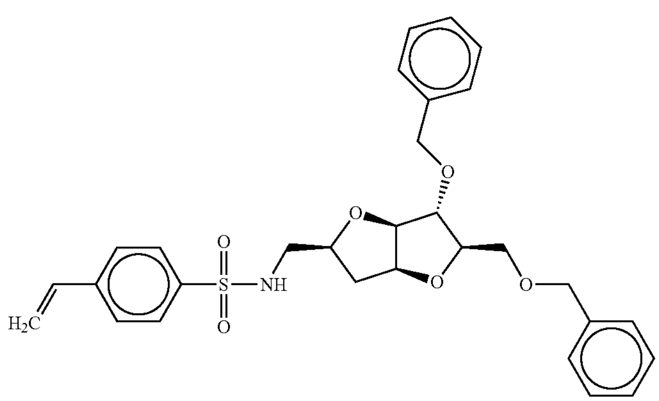 |

TABLE 1-continued

| Compound Number | Structure |
| --- | --- |
| I-15 | 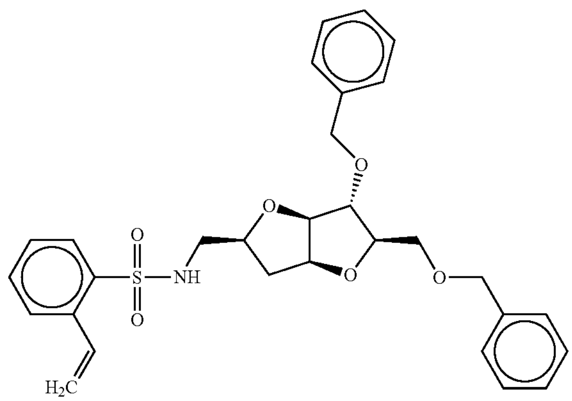 |
| I-16 | 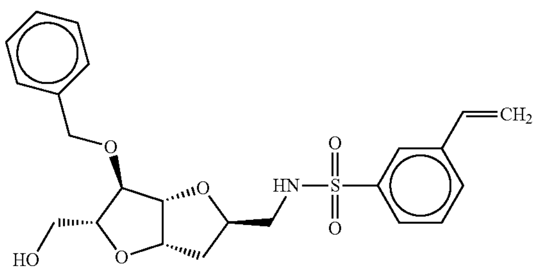 |
| I-17 | 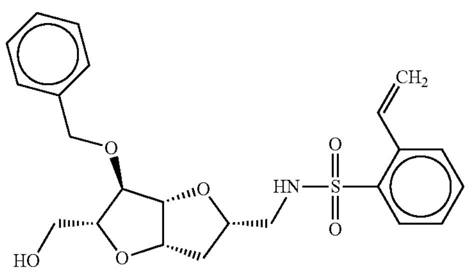 |
| I-18 | 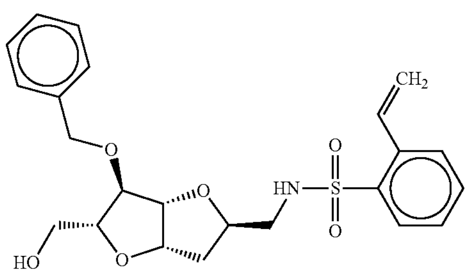 |
| I-19 | 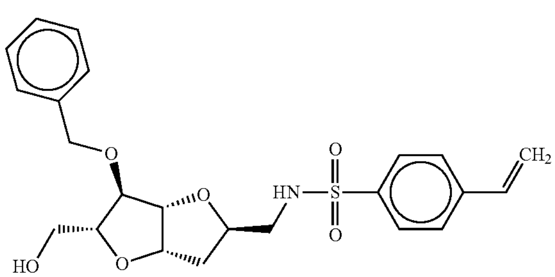 |

TABLE 1-continued

| Compound Number | Structure |
|---|---|
| I-20 | 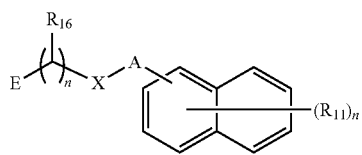 |

In some embodiments, the invention provides compounds of Formula II

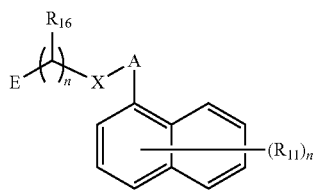

Formula II

In some embodiments the compound of Formula II may have Formula IIa or Formula IIb.

Formula IIa

Formula IIb

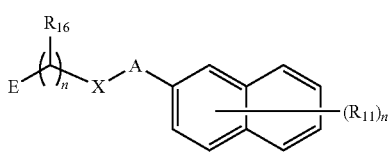

In each of Formula II, IIa and IIb A is a bond, O, $NR_{18}$, S, $CR_{18}R_{19}$, CO, SO or $SO_2$. In some embodiments A is O. In some embodiments A is $NR_{18}$. In some embodiments A is S. In some embodiments A is $CR_{18}R_{19}$. In some embodiments A is CO. In some embodiments A is SO or $SO_2$.

In various embodiments X is bond, $CHR_{17}$, $NR_{17}$, CO, or $SO_2$.

In each of Formula II, IIa and IIb n is a integer between 0 to 6. In some embodiments n is 1. In some embodiments n is 2. In some embodiments n is 3. In some embodiments n is 4. In some embodiments n is 5. In some embodiments n is 6.

$R_{11}$ is halogen, $OR_{12}$, $NR_{13}R_{14}$, alkyl, heteroalkyl, cycloalkyl, cycloheteroalkyl, aryl or heteroaryl moiety each of which is either unsubstituted or substituted with one or more $R_{15}$ groups. In some embodiments $R_{11}$ is halogen. In some embodiments $R_{11}$ is $OR_{12}$. In some embodiments $R_{11}$ is $NR_{13}R_{14}$. In some embodiments $R_{11}$ is an unsubstituted alkyl. In some embodiments $R_{11}$ is an alkyl substituted with one or more $R_{15}$ groups. In some embodiments $R_{11}$ is an unsubstituted heteroalkyl. In some embodiments $R_{11}$ is a heteroalkyl substituted with one or more $R_{15}$ groups. In some embodiments $R_{11}$ is an unsubstituted cycloalkyl. In some embodiments $R_{11}$ is a cycloalkyl substituted with one or more $R_{15}$ groups. In some embodiments $R_{11}$ is an unsubstituted cycloheteroalkyl. In some embodiments $R_{11}$ is a cycloheteroalkyl substituted with one or more $R_{15}$ groups. In some embodiments $R_{11}$ is an unsubstituted aryl. In some embodiments $R_{11}$ is an aryl substituted with one or more $R_{15}$ groups. In some embodiments $R_{11}$ is an unsubstituted heteroaryl. In some embodiments $R_{11}$ is a heteroaryl substituted with one or more $R_{15}$ groups.

$R_{12}$ is halogen, $OR_{12}$, $NR_{13}R_{14}$, alkyl, heteroalkyl, cycloalkyl, cycloheteroalkyl, aryl or heteroaryl moiety each of which is either unsubstituted or substituted with one or more $R_{15}$ groups. In some embodiments $R_{12}$ is halogen. In some embodiments $R_{12}$ is $OR_{12}$. In some embodiments $R_{12}$ is $NR_{13}R_{14}$. In some embodiments $R_{12}$ is an unsubstituted alkyl. In some embodiments $R_{12}$ is an alkyl substituted with one or more $R_{15}$ groups. In some embodiments $R_{12}$ is an unsubstituted heteroalkyl. In some embodiments $R_{12}$ is a heteroalkyl substituted with one or more $R_{15}$ groups. In some embodiments $R_{12}$ is an unsubstituted cycloalkyl. In some embodiments $R_{12}$ is a cycloalkyl substituted with one or more $R_{15}$ groups. In some embodiments $R_{12}$ is an unsubstituted cycloheteroalkyl. In some embodiments $R_{12}$ is a cycloheteroalkyl substituted with one or more $R_{15}$ groups. In some embodiments $R_{12}$ is an unsubstituted aryl. In some embodiments $R_{12}$ is an aryl substituted with one or more $R_{15}$ groups. In some embodiments $R_{12}$ is an unsubstituted heteroaryl. In some embodiments $R_{12}$ is a heteroaryl substituted with one or more $R_{15}$ groups.

$R_{13}$ is halogen, $OR_{12}$, $NR_{13}R_{14}$, alkyl, heteroalkyl, cycloalkyl, cycloheteroalkyl, aryl or heteroaryl moiety each of which is either unsubstituted or substituted with one or more $R_{15}$ groups. In some embodiments $R_{13}$ is halogen. In some embodiments $R_{13}$ is $OR_{12}$. In some embodiments $R_{13}$ is $NR_{13}R_{14}$. In some embodiments $R_{13}$ is an unsubstituted alkyl. In some embodiments $R_{13}$ is an alkyl substituted with one or more $R_{15}$ groups. In some embodiments $R_{13}$ is an unsubstituted heteroalkyl. In some embodiments $R_{13}$ is a heteroalkyl substituted with one or more $R_{15}$ groups. In some embodiments $R_{13}$ is an unsubstituted cycloalkyl. In some embodiments $R_{13}$ is a cycloalkyl substituted with one or more $R_{15}$ groups. In some embodiments $R_{13}$ is an unsubstituted cycloheteroalkyl. In some embodiments $R_{13}$ is a cycloheteroalkyl substituted with one or more $R_{15}$ groups. In some embodiments $R_{13}$ is an unsubstituted aryl. In some embodiments $R_{13}$ is an aryl substituted with one or more $R_{15}$ groups. In some embodiments $R_{13}$ is an unsubstituted heteroaryl. In some embodiments $R_{13}$ is a heteroaryl substituted with one or more $R_{15}$ groups.

$R_{14}$ is halogen, $OR_{12}$, $NR_{13}R_{14}$, alkyl, heteroalkyl, cycloalkyl, cycloheteroalkyl, aryl or heteroaryl moiety each of which is either unsubstituted or substituted with one or more $R_{15}$ groups. In some embodiments $R_{14}$ is halogen. In some embodiments $R_{14}$ is $OR_{12}$. In some embodiments $R_{14}$ is $NR_{13}R_{14}$. In some embodiments $R_{14}$ is an unsubstituted alkyl. In some embodiments $R_{14}$ is an alkyl substituted with one or more $R_{15}$ groups. In some embodiments $R_{14}$ is an unsubstituted heteroalkyl. In some embodiments $R_{14}$ is a heteroalkyl substituted with one or more $R_{15}$ groups. In some embodiments $R_{14}$ is an unsubstituted cycloalkyl. In some embodiments $R_{14}$ is a cycloalkyl substituted with one or more $R_{15}$ groups. In some embodiments $R_{14}$ is an unsubstituted cycloheteroalkyl. In some embodiments $R_{14}$ is a cycloheteroalkyl substituted with one or more $R_{15}$ groups. In some embodiments $R_{14}$ is an unsubstituted aryl. In some embodiments $R_{14}$ is an aryl substituted with one or more $R_{15}$ groups. In some embodiments $R_{14}$ is an unsubstituted heteroaryl. In some embodiments $R_{14}$ is a heteroaryl substituted with one or more $R_{15}$ groups.

In various embodiments $R_{15}$ is hydrogen, halogen, oxo, hydroxy, alkyl, alkoxy, heteroalkyl, cycloalkyl, cycloheteroalkyl, aryl or heteroaryl moiety. In some embodiments $R_{15}$ is hydrogen. In some embodiments $R_{15}$ is halogen. In some embodiments $R_{15}$ is oxo. In some embodiments $R_{15}$ is hydroxy. In some embodiments $R_{15}$ is alkyl. In some embodiments $R_{15}$ is alkoxy. In some embodiments $R_{15}$ is heteroalkyl. In some embodiments $R_{15}$ is cysloalkyl. In some embodiments $R_{15}$ is cycloheteroalkyl. In some embodiments $R_{15}$ is aryl. In some embodiments $R_{15}$ is heteroaryl.

In various embodiments $R_{16}$ is hydrogen, unsubstituted alkyl, alkyl substituted with one or more $R_{20}$ groups, or heterocycloalkyl.

Each of $R_{17}$, $R_{18}$, $R_{19}$, $R_{20}$ in each occurrence are independently hydrogen, halogen, hydroxyl, alkyl, cycloalkyl, heteroalkyl, heterocycloalkyl, aryl, heteroaryl moiety.

In some embodiments E is an electrophile capable of bonding with a K-Ras, H-Ras or N-ras protein comprising G12C mutation. In some embodiments, the electrophile E is capable of forming an irreversible covalent bond with a G12C mutant K-Ras, H-Ras or N-ras protein. In some cases, the electrophile E may bind with the cysteine residue at the position 12 of a G12C mutant K-Ras, H-Ras or N-ras protein. In some embodiments, E is an electrophile capable of forming a covalent bond with a residue near the Switch 2 in G12C mutant K-Ras, H-Ras or N-ras protein. In some embodiments, E is an electrophilic capable of forming a covalent bond with a residue in the Switch 2—Binding Pocket of G12C mutant K-Ras, H-Ras or N-ras protein.

E is an electrophile capable of forming a covalent bond with the cysteine residue at position 12 of a K-Ras, H-Ras or N-ras G12C mutant protein. In some cases E is selected from the group consisting of

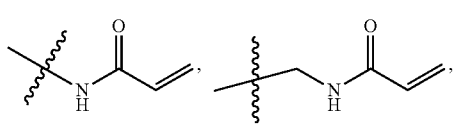

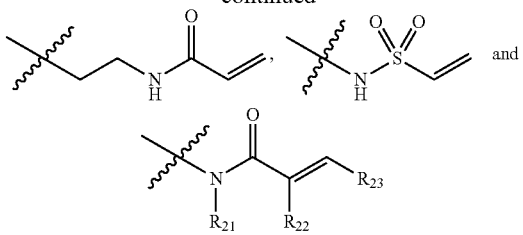

$R_{21}$ = alkyl; $R_{22}$ = CN, alkyl, $R_{23}$ = alkyl; or
$R_{22}$ and $R_{23}$ can form cyclo alkene, aryl or cyclo alkane.

In some embodiments E is

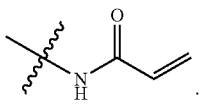 [SMILES: *NC(=O)C=C]

In some embodiments E is

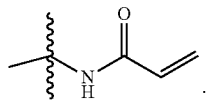 [SMILES: *NC(=O)C=C]

In some embodiments E is

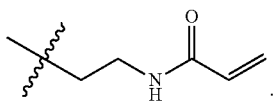 [SMILES: *CCNC(=O)C=C]

In some embodiments E is

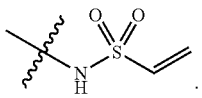

In other embodiments, E is

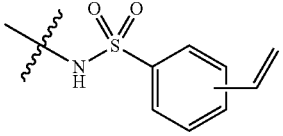

In some embodiments the invention provides compounds of Formula II shown in Table II.

TABLE II

| Compound Number | Structure |
|---|---|
| II-1 | ![structure] |

TABLE II-continued

| Compound Number | Structure |
|---|---|
| II-2 | (vinyl sulfonamide-ethyl-O-naphthalene) |
| II-3 | (vinyl sulfonamide-ethyl-NH-naphthalene) |
| II-4 | (vinyl sulfonamide-ethyl-NH-2-naphthalene) |
| II-5 | (4-vinylphenyl sulfonamide-ethyl-NH-2-naphthalene) |
| II-6 | (4-vinylphenyl sulfonamide-ethyl-O-2-naphthalene) |
| II-7 | (3-vinylphenyl sulfonamide-ethyl-O-1-naphthalene) |

TABLE II-continued
| Compound Number | Structure |
| --- | --- |
| II-8 | 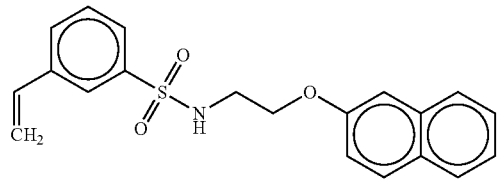 |
| II-9 | 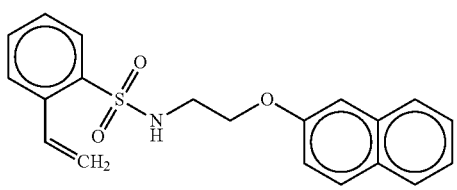 |
| II-10 | 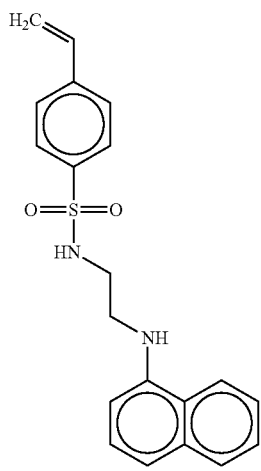 |
| II-11 | 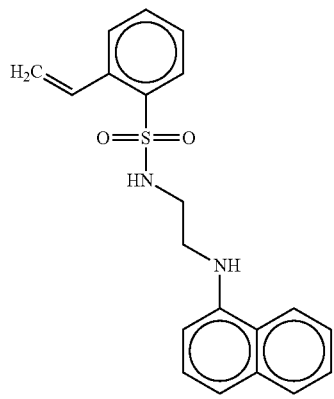 |

TABLE II-continued

| Compound Number | Structure |
|---|---|
| II-12 | 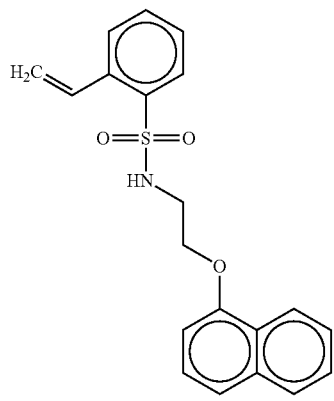 |
| II-13 | 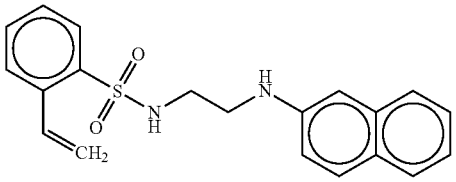 |

In some embodiments, the substituted or unsubstituted napthyl moiety of Formula II (IIa and IIb) may be capable of reversible interaction with K-Ras, H-Ras or N-ras G12C mutant protein. In some embodiments the substituted or unsubstituted napthyl moiety may have high affinity towards K-Ras, H-Ras or N-ras and may be highly specific towards G12C K-Ras, H-Ras or N-ras. In some embodiments the substituted or unsubstituted napthyl moiety is capable of hydrophobic interaction with K-Ras, H-Ras or N-ras G12C. In some embodiments the substituted or unsubstituted napthyl moiety may be able to form hydrogen bonds with various residues of G12C K-Ras, H-Ras or N-ras protein. In some embodiments the substituted or unsubstituted napthyl moiety may interact with one or more of G10, R68, Y71, Y96 or Q99 residues in K-Ras G12C (FIG. 1). In some embodiments the substituted or unsubstituted napthyl moiety interacts with the G10 residue of K-Ras G12C. In some embodiments the substituted or unsubstituted napthyl moiety interacts with the R68 residue of K-Ras G12C. In some embodiments the substituted or unsubstituted napthyl moiety interacts with the Y71 residue of K-Ras G12C. In some embodiments the substituted or unsubstituted napthyl moiety interacts with the Y96 residue of K-Ras G12C. In some embodiments $R_1$ interacts with the Q99 residue of K-Ras G12C.

In some embodiments, the unit in Formula II (IIa and IIb) may provide proper length and geometry to the compound such that the electrophile E may be able to interact with the cysteine residue at the 12 position in G12C K-Ras, H-Ras or N-ras protein. In some embodiments the may also interact with other protein backbone residues.

Pharmaceutical Compositions

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

Pharmaceutical Compositions/Formulations

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins, 1999).

Provided herein are pharmaceutical compositions comprising a compound of any of Formula I or Formula II (IIa or IIb) and a pharmaceutically acceptable diluent(s), excipient(s), or carrier(s). In certain embodiments, the compounds described are administered as pharmaceutical compositions in which compounds of any of Formula I or Formula II (IIa or IIb), are mixed with other active ingredients, as in combination therapy. Encompassed herein are all combinations of actives set forth in the combination therapies section below and throughout this disclosure. In specific embodiments, the pharmaceutical compositions include one or more compounds of any of Formula I or Formula II (IIa or IIb).

A pharmaceutical composition, as used herein, refers to a mixture of a compound of any of Formula I or Formula II (IIa or IIb), with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of any of Formula I or Formula II (IIa or IIb), provided herein are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of any of Formula I or Formula II (IIa or IIb), is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of any of Formula I or Formula II (IIa or IIb), is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including compounds of any of Formula I or Formula II (IIa or IIb), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of any of Formula I or Formula II (IIa or IIb), are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of any of Formula I or Formula II (IIa or IIb), are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of any of Formula I or Formula II (IIa or IIb), are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of any of Formula I or Formula II (IIa or IIb), is accomplished by means of iontophoretic patches and the like. In certain embodiments, transdermal patches provide controlled delivery of the compounds of any of Formula I or Formula II (IIa or IIb). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of any of Formula I or Formula II (IIa or IIb), are formulated for administration by inhalation. Various forms suitable for administration by inhalation include, but are not limited to, aerosols, mists or powders. Pharmaceutical compositions of any of Formula I or Formula II (IIa or IIb), are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of any of Formula I or Formula II (IIa or IIb), are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of any of Formula I or Formula II (IIa or IIb), are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of any of Formula I or Formula II (IIa or IIb), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of any of Formula I or Formula II (IIa or IIb), illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspension contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of any of Formula I or Formula II (IIa or IIb). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g-0.15 g, 0.2 g-0.25 g, 0.3 g-0.35 g, 0.4 g-0.45 g, 0.5 g, 0.55 g, 0.6 g-0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products Include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, Compositions containing a compound provided herein formulated in a compatible pharmaceutical carrier are prepared, placed in an appropriate container, and labeled for treatment of an indicated condition.

Method of Using the Compositions Disclosed Herein

The present invention provides a method of inhibiting Ras-mediated cell signaling comprising contacting a cell with an effective amount of one or more compounds disclosed herein Inhibition of Ras-mediated signal transduction can be assessed and demonstrated by a wide variety of ways known in the art. Non-limiting examples include a showing of (a) a decrease in GTPase activity of Ras; (b) a decrease in GTP binding affinity or an increase in GDP binding affinity; (c) an increase in $K_{off}$ of GTP or a decrease in $K_{off}$ of GDP; (d) a decrease in the levels of signaling transduction molecules downstream in the Ras pathway, such as a decrease in pMEK level; and/or (e) a decrease in binding of Ras complex to downstream signaling molecules including but not limited to Raf. Kits and commercially available assays can be utilized for determining one or more of the above.

The invention also provides methods of using the compounds or pharmaceutical compositions of the present invention to treat disease conditions, including but not limited to conditions implicated by G12C K-Ras, H-Ras or N-ras mutation.

In some embodiments, a method for treatment of cancer is provided, the method comprising administering an effective amount of any of the foregoing pharmaceutical compositions comprising a compound of structure (I) to a subject in need thereof. In some embodiments, the cancer is mediated by a k-ras, H-Ras or N-ras G12C mutation. In other embodiments, the cancer is pancreatic cancer, colon cancer, MYH associated polyposis, colorectal cancer or lung cancer.

In some embodiments the invention provides method of treating a disorder in a subject in need thereof, wherein the said method comprises determining if the subject has a K-Ras, H-Ras or N-ras G12C mutation and if the subject is determined to have the K-Ras, H-Ras or N-ras G12C mutation, then administering to the subject a therapeutically effective dose of at least one compound of Formula I or Formula II (IIa or IIb), or a pharmaceutically acceptable salt, ester, prodrug, solvate, hydrate or derivative thereof.

The disclosed compounds strongly inhibit anchorage-independent cell growth and therefore have the potential to inhibit tumor metastasis. Accordingly, in another embodiment the disclosure provides a method for inhibiting tumor metastasis, the method comprising administering an effective amount a pharmaceutical composition of comprising any of the compounds disclosed herein and a pharmaceutically acceptable carrier to a subject in need thereof.

K-Ras, H-Ras or N-ras G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkin's lymphoma or non-Hodgkin's lymphoma.

Determining whether a tumor or cancer comprises a G12C K-ras, H-Ras or N-ras mutation can be undertaken by assessing the nucleotide sequence encoding the K-ras, H-Ras or N-ras protein, by assessing the amino acid sequence of the K-ras, H-Ras or N-ras protein, or by assessing the characteristics of a putative K-ras, H-Ras or N-ras mutant protein. The sequence of wild-type human K-Ras is known in the art, (e.g., Accession No. NP203524).

Methods for detecting a mutation in a K-ras, H-Ras or N-ras nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples may be evaluated for G12C K-ras, H-Ras or N-ras mutations by real-time PCR. In real-time PCR, fluorescent probes specific for the K-Ras, H-Ras or N-ras G12C mutation are used. When a mutation is present, the probe binds and fluorescence is detected. In some embodiments, the K-Ras, H-Ras or N-ras G12C mutation may be identified using a direct sequencing method of specific regions (e.g., exon 2 and/or exon 3) in the k-ras, H-Ras or N-ras gene. This technique will identify all possible mutations in the region sequenced.

Methods for detecting a mutation in a K-ras, H-Ras or N-ras protein are known by those of skill in the art. These methods include, but are not limited to, detection of a K-ras, H-Ras or N-ras mutant using a binding agent (e.g., an antibody) specific for the mutant protein, protein electrophoresis and Western blotting, and direct peptide sequencing.

Methods for determining whether a tumor or cancer comprises a G12C K-ras, H-Ras or N-ras mutation can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In certain particular embodiments, the invention relates to methods for treatment of lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with compounds of the invention, or pharmaceutically acceptable salt, ester, prodrug, solvate, hydrate or derivative of said compounds, according to the methods of this invention include, for example, subjects that have been diagnosed as having acute myeloid leukemia, acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments subject that may be treated with the compounds of the invention include subjects that have been diagnosed as having a non-cancerous hyperproliferative disorder such as benign hyperplasia of the skin (e.g., psoriasis), restenosis, or prostate (e.g., benign prostatic hypertrophy (BPH)).

The invention further provides methods of modulating a G12C Mutant KRas, H-Ras or N-ras protein activity by contacting the protein with an effective amount of a compound of the invention. Modulation can be inhibiting or activating protein activity. In some embodiments, the invention provides methods of inhibiting protein activity by contacting the G12C Mutant Kras, H-Ras or N-ras protein with an effective amount of a compound of the invention in solution. In some embodiments, the invention provides methods of inhibiting the G12C Mutant Kras, H-Ras or N-ras protein activity by contacting a cell, tissue, organ that express the protein of interest. In some embodiments, the invention provides methods of inhibiting protein activity in subject including but not limited to rodents and mammal (e.g., human) by administering into the subject an effective amount of a compound of the invention. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the invention provides methods of inhibiting K-Ras, H-Ras or N-ras G12C activity in a cell by contacting said cell with an amount of a compound of the invention sufficient to inhibit the activity of K-Ras, H-Ras or N-ras G12C in said cell. In some embodiments, the invention provides methods of inhibiting K-Ras, H-Ras or N-ras G12C activity in a tissue by contacting said tissue with an amount of a compound of the invention sufficient to inhibit the activity of K-Ras, H-Ras or N-ras G12C in said tissue. In some embodiments, the invention provides methods of inhibiting K-Ras, H-Ras or N-ras G12C activity in an organism by contacting said organism with an amount of a compound of the invention sufficient to inhibit the activity of K-Ras, H-Ras or N-ras G12C in said organism. In some embodiments, the invention provides methods of inhibiting K-Ras, H-Ras or N-ras G12C activity in an animal, including humans by contacting said animal with an amount of a compound of the invention sufficient to inhibit the activity of K-Ras, H-Ras or N-ras G12C in said animal. In some embodiments, the invention provides methods of inhibiting K-Ras, H-Ras or N-ras G12C activity in a mammal by contacting said mammal with an amount of a compound of the invention sufficient to inhibit the activity of K-Ras, H-Ras or N-ras G12C in said mammal. In some embodiments, the invention provides methods of inhibiting K-Ras, H-Ras or N-ras G12C activity in a human by contacting said human with an amount of a compound of the invention sufficient to inhibit the activity of K-Ras, H-Ras or N-ras G12C in said human. The present invention provides methods of treating a disease mediated by K-Ras, H-Ras or N-ras G12C activity in a subject in need of such treatment.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of one or more compounds of the invention with chemotherapeutic agents, therapeutic antibodies, and radiation treatment, to provide a synergistic or additive therapeutic effect.

Many chemotherapeutics are presently known in the art and can be used in combination with the compounds of the invention. In some embodiments, the chemotherapeutic is selected from the group comprising of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126, and Zosuquidar.

This invention further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

The invention also relates to a method of and to a pharmaceutical composition for treating a cardiovascular disease in a mammal which comprises an amount of a compound of the invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds described herein may be formulated or administered in conjunction with liquid or solid tissue barriers also known as lubricants. Examples of tissue barriers include, but are not limited to, polysaccharides, polyglycans, seprafilm, intercede and hyaluronic acid.

Medicaments which may be administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments may be used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a compound of the invention include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention including but not limited to compound 1 of Table 1 with sorafenib and/or avastin. For treating an endometrial disorder, one may combine a compound of the present invention including but not limited to compound 1 of Table 1 with doxorubincin, taxotere (taxol), and/or cisplatin (carboplatin). For treating ovarian cancer, one may combine a compound of the present invention including but not limited to compound 1 of Table 1 with cisplatin (carboplatin), taxotere, doxorubincin, topotecan, and/or tamoxifen. For treating breast cancer, one may combine a compound of the present invention including but not limited to compound 1 of Table 1 with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention including but not limited to compound 1 of Table 1 with taxotere (taxol), gemcitabine, cisplatin, pemetrexed, Tarceva, PD0325901, and/or avastin.

Further therapeutic agents that can be combined with a compound of the invention may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administered with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In the separate administration protocol, a compound of the invention and any of the agents described above may be administered a few minutes apart, or a few hours apart, or a few days apart.

Administration

Administration of the compounds of the present invention can be effected by any method that enables delivery of the compounds to the site of action. An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parentally, intramuscularly, subcutaneously, orally, topically, as an inhalant, or via an impregnated or coated device such as a stent, for example, or an artery-inserted cylindrical polymer.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

When a compound of the invention, is administered in a composition that comprises one or more agents, and the agent has a shorter half-life than the compound of the invention, unit dose forms of the agent and the compound of the invention may be adjusted accordingly.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

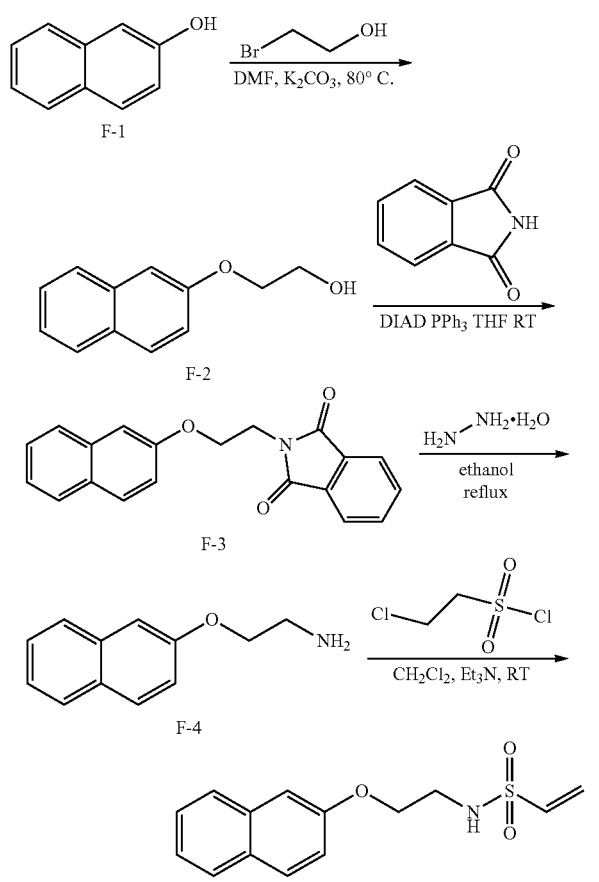

2-(Naphthalen-2-yloxy)ethanol

To a stirred solution of naphthalen-2-ol (4 g, 28 mmol) and K$_2$CO$_3$ (9.7 g, 70 mmol) in DMF (200 mL), 2-bromoethanol (3.8 g, 31 mmol) was added dropwise and the resulting the mixture was stirred at 80° C. overnight. The mixture was partitioned between water and ethyl acetate. The organic layer was washed with brine (150 mL×2), dried over Na$_2$SO$_4$ and concentrated in vacuo. The residue was purified by flash column chromatography on silica gel (petroleum ether/ethyl acetate=10:1) to afford the desired product (3.5 g, 67% yield) as an oil.

2-(2-(Naphthalen-1-yloxy)ethyl)isoindoline-1,3-dione

A mixture of 2-(naphthalen-1-yloxy)ethanol (12 g, 63.8 mmol), isoindoline-1,3-dione (14.1 g, 96 mmol) and PPh$_3$ (25 g, 96 mmol) in THF (150 mL) at room temperature, DIAD (19.3 g, 96 mmol) was added and the resulting mixture was stirred for 16 h. The mixture was partitioned between water and ethyl acetate. The organic layer was washed with brine, dried over Na$_2$SO$_4$ and concentrated in vacuo. The residue was purified by flash column chromatography on silica gel (petroleum ether/ethyl acetate=8:1) to afford the desired product (10 g, 50% yield).

2-(Naphthalen-1-yloxy)ethanamine

To a stirred solution of 2-(2-(naphthalen-1-yloxy)ethyl)isoindoline-1,3-dione (6 g, 18.6 mmol) in ethanol (100 mL), hydrazine hydrate (4.7 g, 94.5 mmol) was added dropwise and the resulting mixture was stirred at reflux for 1 h. The resulting mixture was concentrated in vacuo to remove the solvent, and the residue was dissolved in ethyl acetate. The organic layer was washed with HCl (aq, 10%), water and brine, dried over Na$_2$SO$_4$, and then concentrated in vacuo. The residue was purified by flash column chromatography on silica (dichloromethane/methanol=20:1) to afford the desired product (3.4 g, 94% yield).

N-(2-(Naphthalen-1-yloxy)ethyl)-4-vinylbenzenesulfonamide

To a stirred solution of 2-(naphthalen-1-yloxy) ethanamine (300 mg, 1.6 mmol) and triethylamine (243 mg, 2.4 mmol) in DCM (15 mL), 4-vinylbenzene-1-sulfonyl chloride (357 mg, 1.6 mmol) was added dropwise and the resulting mixture was stirred at room temperature for 16 h. The mixture was concentrated in vacuo. The residue was purified by flash column chromatography on silica (petroleum ether/ethyl acetate=4:1) to afford the desired product (450 mg, 82% yield). $^1$H NMR (400 MHz, DMSO-d6) δ: 8.90 (s, 1H), 7.85-7.81 (m, 2H), 7.67-7.64 (m, 1H), 7.49-7.47 (m, 1H), 7.38-7.33 (m, 2H), 7.20-7.17 (dd, J=2.8, 9.2 Hz, 1H), 6.82-6.75 (m, 1H), 6.10-6.06 (d, J=16.4 Hz, 1H), 6.00-5.98 (d, J=10.0 Hz, 1H), 4.17-4.14 (t, J=5.6 Hz, 2H), 3.35-3.28 (m, 2H). ESI-MS m/z: 276.2 [M–H]$^-$.

Example 2

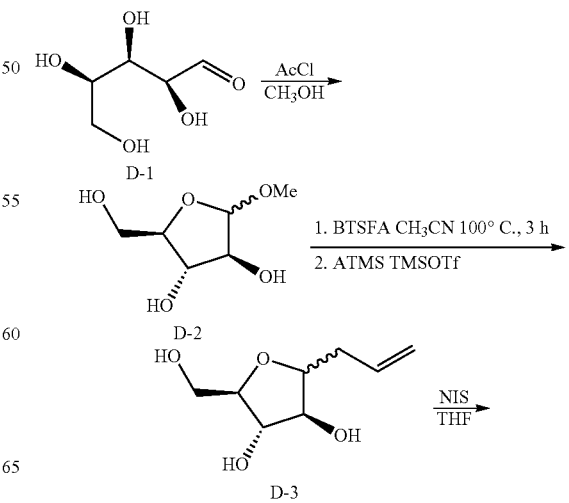

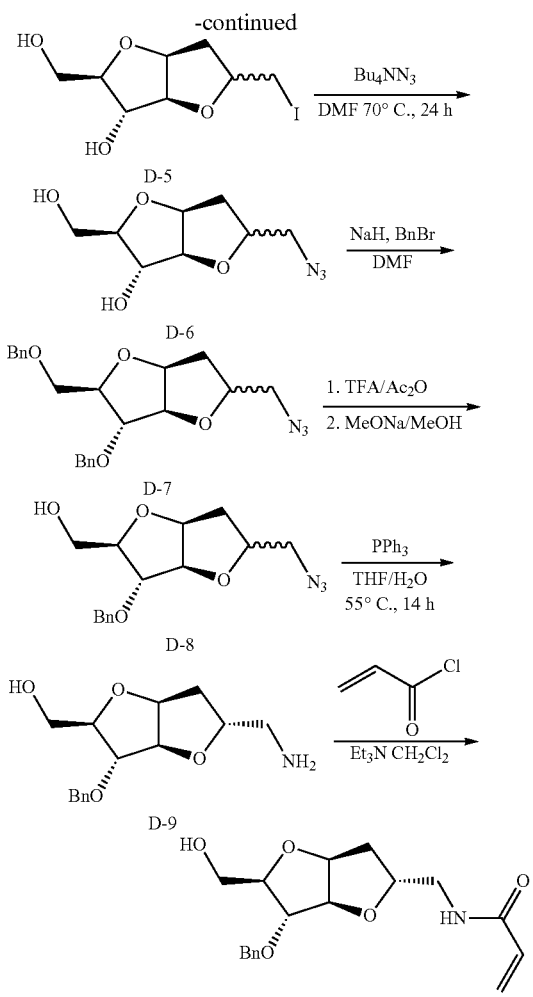

Methyl D-arabinofuranoside

To a stirred suspension of D-arabinose (10 g, 66.7 mmol) in dry methanol (380 mL), acetyl chloride was added dropwise at room temperature under argon. After 24 h, Amberlite IRN78 OH— resin was added to neutralize the acid, and the resulting mixture was stirred for 5 min. The resin was removed by filtration, and the filtrate was concentrated in vacuo. The residue was purified by flash column chromatography on silica gel (ethyl acetate/methanol=40:1) afforded desired product (8.95 g, 82% yield) as a yellow oil. (a mixture of diastereomers, R and S).

1-(D-Arabinofuranosyl)-2-propene

To a stirred solution of methyl D-arabinofuranoside (6 g, 36.5 mmol) in dry CH$_3$CN (10 mL) at 100° C. under argon, BTSFA (20 mL, 80.5 mmol) was added and the resulting mixture was stirred for 3 h. The mixture was allowed to cool to 0° C., and then ATMS (8.6 mL, 54.75 mmol) and trimethylsilyl trifluoromethanesulfonate (TMSOTf) (3.3 mL, 18.25 mmol) were added. The resulting mixture was stirred at room temperature for 1 h. Water (120 mL) was added slowly to hydrolyze TMS ethers. The mixture was neutralized with 1M NaOH aqueous solution (100 mL), and concentrated in vacuo. The residue was purified by flash column chromatography on silica gel (petroleum ether/ethyl acetate=1:9) to afford the desired product (5.2 g, 82% yield) as a light green oil. (a mixture of diastereomers).

(2R,3R,3aS,6aS)-Hexahydro-2-(hydroxymethyl)-5-(iodomethyl)furo[3,2-b]furan-3-ol

To a stirred solution of 1-(D-Arabinofuranosyl)-2-propene (5.2 g, 30 mmol) in dry THF (200 mL) at 90° C. under argon, NIS (10.1 g, 45 mmol) was added. After 10 min, the mixture was cooled to room temperature, saturated Na$_2$S$_2$O$_3$ aqueous solution was added to quench excess iodine, and the suspension was vigorously stirred until it became colorless. The residue was purified by flash column chromatography on silica gel (petroleum ether/ethyl acetate=1:4) to afford the desired product (7 g, 58% yield) as a light green oil. (a mixture of diastereomers).

(2R,3R,3aS,6aS)-5-(Azidomethyl)-hexahydro-2-(hydroxymethyl)furo[3,2-b]furan-3-ol To a stirred solution of (2R,3R,3aS,6aS)-hexahydro-2-(hydroxymethyl)-5-(iodomethyl)furo[3,2-b]furan-3-ol (5 g, 16.6 mmol) in dry toluene (50 mL) at 70° C. under argon, tetrabutylammonium azide (5.21 g, 18.2 mmol) was added. After 24 h, the reaction mixture was concentrated in vacuo to afford the crude product (2.34 g, 65% yield) as a yellow oil. (a mixture of diastereomers).

(2R,3R,3 aR,6aS)-5-(Azidomethyl)-3-(benzyloxy)-2-((benzyloxy)methyl)-hexahydrofuro[3,2-b]furan To a stirred solution of compound (2R,3R,3aS,6aS)-5-(azidomethyl)-hexahydro-2-(hydroxymethyl)furo[3,2-b]furan-3-ol (2.34 g, 10.81 mmol) in dry DMF at room temperature, benzyl bromide (7.34 g, 43.5 mmol) and NaH (60% in oil, 1.7 g, 43.5 mmol) were added in three portions over a period of 20 min. The mixture was stirred for 15 min, quenched by adding ethanol and then concentrated in vacuo. The residue was purified by flash column chromatography on silica gel (petroleum ether/ethyl acetate=12:1) to afford the desired product (3.1 g, 73% yield) as a yellow oil (a mixture of diastereomers).

((3aS,5R,6R,6aR)-2-(Azidomethyl)-6-(benzyloxy)-hexahydrofuro[3,2-b]furan-5-yl)methanol A solution of compound (2R,3R,3aR,6aS)-5-(azidomethyl)-3-(benzyloxy)-2-((benzyloxy)methyl)-hexahydrofuro[3,2-b]furan (3.1 g, 7.8 mmol) in Ac$_2$O/TFA (16 mL, 4:1) was stirred at room temperature for 90 min. The reaction was quenched by adding a mixture of ice and 1M NaOH aqueous solution (100 mL) and then extracted with ethyl acetate. After the usual workup, the obtained crude mixture was dissolved in dry MeOH (40 mL) and metallic Na (1.2 g, 52.2 mmol) was added under argon. The solution was stirred at room temperature for 30 min. Amberlite IRA-120 H+ resin was added, and the mixture was stirred for 10 min. The resin was removed by filtration, and the filtrate was concentrated in vacuo. After the usual workup and flash column chromatography on silica gel (petroleum ether/ethyl acetate=5:1) to afford the desired product (1.54 g, 86% yield) as a mixture of diastereomers.

((2R,3aS,5R,6R,6aR)-2-(Aminomethyl)-6-(benzyloxy)-hexahydrofuro[3,2-b]furan-5-yl)methanol To a solution of this diastereomeric mixture of ((3aS,5R, 6R,6aR)-2-(azidomethyl)-6-(benzyloxy)-hexahydrofuro[3, 2-b]furan-5-yl)methanol (1.54 g, 5 mmol) in THF (60 mL), triphenylphosphane (5.29 g, 20 mmol) and water (3 mL, 59 mmol) were added, and the reaction mixture was stirred at 60° C. for 14 h. The reaction mixture was concentrated in vacuo. The residue was purified by flash column chromatography on silica gel (dichloromethane/methanol=50:1 with 1% NH$_4$OH) to afford the desired product (1.2 g, 86% yield) as colorless oil. (a mixture of diastereomers).

N-(((2R,3R,3aR,5R,6aS)-3-(Benzyloxy)-hexahydro-2-(hydroxymethyl)furo[3,2-b]furan-5-yl)methyl)acrylamide To a stirred solution of ((2R,3aS,5R,6R,6aR)-2-(aminomethyl)-6-(benzyloxy)-hexahydrofuro[3,2-b]furan-5-yl)methanol (150 mg, 0.53 mmol) in dry dichloromethane (10 mL) at 0° C. under argon, Et$_3$N (65 mg, 0.65 mmol) and acryloyl chloride (48 mg, 0.53 mmol) were added and the resulting mixture was stirred for 2 h. The reaction mixture was quenched with MeOH and then concentrated in vacuo. The residue was purified by flash column chromatography on silica gel (dichloromethane/methanol=50:1) to afford the desired product (150 mg, 90% yield). $^1$H NMR (400 MHz, CDCl$_3$) δ: 7.41-7.27 (m, 5H), 6.33 (d, J=16.8 Hz, 1H), 6.13 (dd, J=10, 16.8 Hz, 1H), 5.88 (bs, 1H), 5.70 (d, J=10.4 Hz, 1H), 4.75 (m, 2H), 4.60 (m, 2H), 4.21 (m, 1H), 3.89 (m, 2H), 3.84 (m, 1H) 3.68 (m, 1H), 3.41 (m, 1H), 2.17 (dd, J=5.2, 13.6 Hz, 1H), 1.84 (m, 1H), 1.44 (m, 1H). ESI-MS m/z: 356.15 [M+Na]$^+$.

Example 3

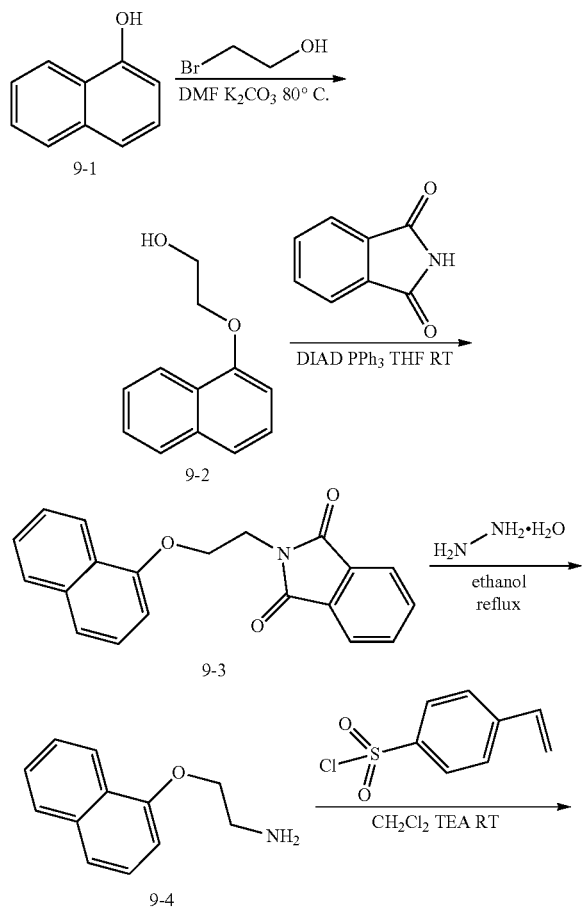

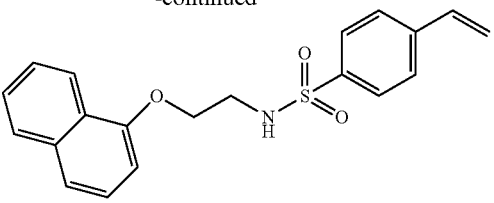

2-(Naphthalen-1-yloxy)ethanol

To a stirred solution of naphthalen-1-ol (10 g, 67.9 mmol) and K$_2$CO$_3$ (23.5 g, 169.8 mmol) in DMF (150 mL), 2-bromoethanol (9.3 g, 74.7 mmol) was added dropwise. The reaction mixture was stirred at 80° C. for 16 h. The resulting mixture was diluted with water and extracted with ethyl acetate. The organic layer was washed with water and brine, dried over Na$_2$SO$_4$, and concentrated in vacuo. The residue was purified by flash column chromatography on silica gel (petroleum ether/ethyl acetate 6:1) to afford the desired product (14 g, 67% yield).

2-(2-(Naphthalen-2-yloxy)ethyl)isoindoline-1,3-dione

To a mixture of 2-(naphthalen-2-yloxy)ethanol (6 g, 32 mmol), isoindoline-1,3-dione (14.1 g, 96 mmol) and PPh$_3$ (25 g, 96 mmol) in THF (300 mL) at room temperature, DIAD (19.3 g, 96 mmol) was added and the resulting mixture was stirred for 16 h. The mixture was poured into water and extracted with ethyl acetate. The organic layer was washed with water and brine, dried over Na$_2$SO$_4$ and concentrated in vacuo. The residue was purified by flash column chromatography on silica gel (petroleum ether/ethyl acetate=6:1) to afford the desired product (4 g, 41% yield).

2-(Naphthalen-2-yloxy)ethanamine

To a stirred solution of 2-(2-(naphthalen-2-yloxy)ethyl)isoindoline-1,3-dione (4 g, 12.6 mmol) in ethanol (50 mL), hydrazine hydrate (3.2 g, 63 mmol) was added dropwise and the resulting mixture was stirred at reflux for 30 min. The mixture was allowed to cool to room temperature and then concentrated in vacuo. The residue was dissolved in ethyl acetate, washed with HCl (aq, 10%), water and brine. The organic layer was dried over Na$_2$SO$_4$ and concentrated in vacuo. The residue was purified by flash column chromatography on silica (petroleum ether/ethyl acetate=4:1) to afford the desired product (2 g, 87% yield).

N-(2-(Naphthalen-2-yloxy)ethyl)ethenesulfonamide

To a stirred solution of 2-(naphthalen-2-yloxy)ethanamine (500 mg, 2.67 mmol) and triethylamine (405 mg, 4 mmol) in DCM (15 mL), 2-chloroethanesulfonyl chloride (435 mg, 2.67 mmol) was added dropwise and the resulting mixture was stirred at room temperature for 16 h. The mixture was concentrated in vacuo and the residue was purified by flash column chromatography on silica gel (petroleum ether/ethyl acetate=6:1) to afford the desired product (160 mg, 22% yield). $^1$H NMR (400 MHz, DMSO-d6) δ: 8.89 (s, 1H), 8.17-8.15 (m, 1H), 8.13-8.10 (m, 1H), 7.84-7.82 (d, J=5.6 Hz, 2H), 7.67-7.64 (d, J=8.8 Hz, 2H), 7.55-7.53 (m, 1H), 7.47-7.45 (d, J=8.0 Hz, 2H), 7.45-7.37 (m, 1H), 6.88-6.86 (d, J=7.2 Hz, 1H), 6.85-6.78 (m, 1H), 6.01-5.97 (d, J=17.6 Hz, 1H), 5.46-5.43 (d, J=11.2 Hz, 1H), 4.14-4.11 (m, 2H), 3.35-3.23 (m, 2H). ESI-MS m/z: 354.1 [M+H]+.

Example 4

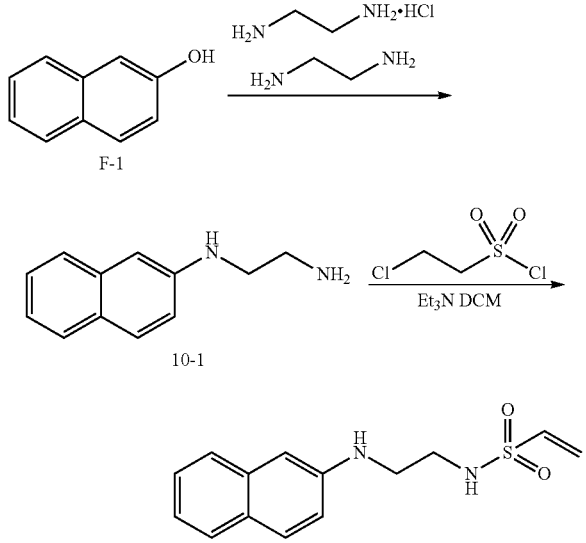

N1-(Naphthalen-2-yl)ethane-1,2-diamine

A mixture of naphthalen-2-ol (2.88 g, 20 mmol), ethane-1,2-diamine hydrochloride (3.5 g, 26.3 mmol) and ethane-1,2-diamine (8 g, 13 3 mmol) in a sealed tube was stirred at 160° C. for 24 h. The mixture was allowed to cool to room temperature, and then partitioned between aqueous $Na_2CO_3$ solution (150 mL) and ethyl acetate. The combined organic layer was dried over $Na_2SO_4$, filtered and concentrated in vacuo. The residue was purified by flash column chromatography on silica (dichloromethane/methanol/$NH_3 \cdot H_2O$=200:10:0.5) to afford the desired product (640 mg, 18% yield). ESI-MS m/z: 187.5 [M+H]+.

N-(2-(Naphthalen-2-ylamino)ethyl)ethenesulfonamide

To a stirred solution of N1-(naphthalen-2-yl)ethane-1,2-diamine (80 mg, 0.43 mmol) and triethylamine (0.5 mL, 0.36 mmol) in DCM (15 mL), 2-chloroethanesulfonyl chloride (77 mg, 0.47 mmol) was added dropwise and the resulting mixture was at room temperature for 16 h. The mixture was concentrated in vacuo and the residue was purified by flash column chromatography on silica (petroleum ether/ethyl acetate=4:1) to afford the desired product (17 mg, 14% yield). 1H NMR (400 MHz, $CDCl_3$) δ: 7.71-7.62 (m, 3H), 7.41-7.38 (m, 1H), 7.28 (s, 1H), 7.27-7.23 (m, 1H), 6.93-6.90 (dd, J=2.4, 8.8 Hz, 1H), 6.85-6.84 (d, J=2.4 Hz, 1H), 6.56-6.50 (m, 1H), 6.31-6.27 (d, J=16.4 Hz, 1H), 5.96-5.94 (d, J=9.6 Hz, 1H), 4.77-4.74 (m, 1H), 3.49-3.46 (m, 2H), 3.37-3.33 (m, 2H). ESI-MS m/z: 277.1 [M+H]+.

Example 5

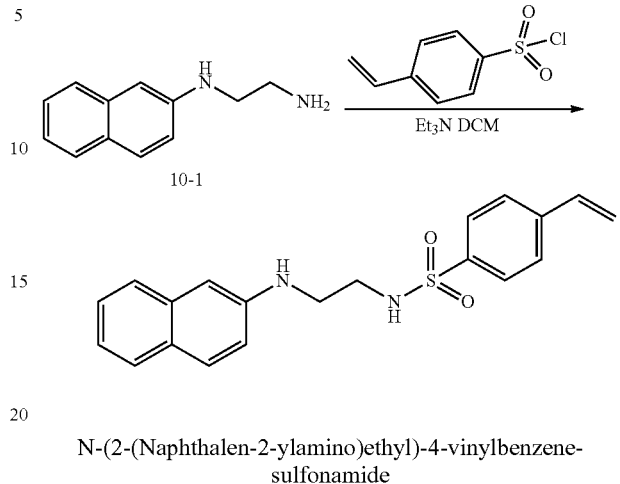

N-(2-(Naphthalen-2-ylamino)ethyl)-4-vinylbenzenesulfonamide

To a stirred solution of N1-(naphthalen-2-yl)ethane-1,2-diamine (100 mg, 0.54 mmol) and triethylamine (164 mg, 1.62 mmol) in DCM (15 mL), 4-vinylbenzene-1-sulfonyl chloride (109 mg, 0.54 mmol) was added dropwise and the resulting mixture was stirred at room temperature for 16 h. The mixture was concentrated in vacuo and the residue was purified by flash column chromatography on silica gel (petroleum ether/ethyl acetate=8:1) to afford the desired product (55 mg, 29% yield). 1H NMR (400 MHz, $CDCl_3$) δ: 7.85-7.82 (d, J=8.0 Hz, 1H), 7.70-7.5 (m, 3H), 7.49-7.47 (d, J=8.4 Hz, 1H), 7.41-7.37 (m, 1H), 7.29-7.24 (m, 2H), 6.92-6.89 (dd, J=4.0, 4.8 Hz, 1H), 6.85 (s, 1H), 6.76-6.69 (m, 1H), 5.88-5.84 (d, J=18.0 Hz, 1H), 5.45-5.43 (d, J=10.8 Hz, 1H), 5.18 (m, 1H), 3.45-3.42 (m, 2H), 3.33-3.28 (m, 2H). ESI-MS m/z: 353.1 [M+H]+.

Example 15

Biochemical Assay of the Compounds

Test compounds were prepared as 10 mM stock solutions in DMSO (Fisher cat# BP-231-100). KRAS G12C 1-169, his-tagged protein, GDP-loaded was diluted to 2 µm in buffer (20 mM Hepes, 150 mM NaCl, 1 mM $MgCl_2$). Compounds were tested for activity as follows:

Compounds were diluted to 50× final test concentration in DMSO in 96-well storage plates. Compound stock solutions were vortexed before use and observed carefully for any sign of precipitation. Dilutions were as follow:

For 100 µM final compound concentration, compounds were diluted to 5000 µM (5 µl 10 mM compound stock +5 µl DMSO) and mixed well by pipetting.

For 30 µM final compound concentration, compounds were diluted to 1500 µM (3 µl 10 mM compound stock +17 µl DMSO) and mixed well by pipetting.

For 10 µM final compound concentration, compounds were diluted to 500 µM (2 µl 10 mM compound stock +38 µl DMSO) and mixed well by pipetting.

49 µl of the stock protein solution was added to each well of a 96-well PCR plate (Fisher cat#1423027). 1 µl of the diluted 50× compounds were added to appropriate wells in the PCR plate using 12-channel pipettor. Reactions were mixed carefully and thoroughly by pipetting up/down with a 200 μl multi-channel pipettor. The plate was sealed well with aluminum plate seal, and stored in drawer at room temperature for 24 hrs. 5 μl of 2% formic acid (Fisher cat# A117) in DI H$_2$O was then added to each well followed by mixing with a pipette. The plate was then resealed with aluminum seal and stored on dry ice until analyzed as described below.

The above described assays were analyzed by mass spectrometry according to the following procedure:

The MS instrument is set to positive polarity, 2 GHz resolution, and low mass (1700) mode and allowed to equilibrate for 30 minutes. The instrument is then calibrated, switched to acquisition mode and the appropriate method loaded.

After another 30 minute equilibration time, a blank batch (i.e., buffer) is run to ensure equipment is operating properly. The samples are thawed at 37° C. for 10 minutes, briefly centrifuged, and transfer to the bench top. Wells A1 and H12 are spiked with 1 uL 500 uM internal standard peptide, and the plates centrifuged at 2000×g for 5 minutes. The method is then run and masses of each individual well recorded.

The masses (for which integration data is desired) for each well are pasted into the platemap and exported from the analysis. Masses for the internal standards are exported as well. The data at 50 ppm is extracted for the +19 charge state, and identity of well A1 is assigned using the internal standard spike and integrated. Peak data is exported as a TOF list and the above steps are repeated individually, for the +20, 21, 22, 23, 24, and 25 charge states.

Other in vitro analyses were as follows:

Inhibition of Cell Growth:

The ability of the subject compounds to inhibit Ras-mediated cell growth is assessed and demonstrated as follows. Cells expressing a wildtype or a mutant Ras are plated in white, clear bottom 96 well plates at a density of 5,000 cells per well. Cells are allowed to attach for about 2 hours after plating before a compound disclosed herein is added. After certain hours (e.g., 24 hours, 48 hours, or 72 hours of cell growth), cell proliferation is determined by measuring total ATP content using the Cell Titer Glo reagent (Promega) according to manufacturer's instructions. Proliferation EC50s is determined by analyzing 8 point compound dose responses at half-log intervals decreasing from 100 μM.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12V, or G12A) are treated with or without (control cells) a subject compound. Inhibition of Ras signaling by one or more subject compounds is demonstrated by a decrease in the steady-state level of phosphorylated MEK, and/or Raf binding in cells treated with the one or more of the subject compounds as compared to the control cells.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12V, or G12A) are treated with or without (control cells) a subject compound. Inhibition of Ras signaling by one or more subject compounds is demonstrated by percentage binding of compound to the G12C mutated Ras protein in cells treated with the one or more of the subject compounds as compared to the control cells.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12V, or G12A) are treated with or without (control cells) a subject compound. Inhibition of Ras signaling by one or more subject compounds is demonstrated by a decrease in binding of Ras complex to downstream signaling molecules (for example Raf) in cells treated with the one or more of the subject compounds as compared to the control cells.

Each of the compounds in Tables 1 and 2 were tested as described above and found to covalently bind to KRAS G12C. Binding activity of the compounds is presented in Table 3.

TABLE 3

Activity of Representative Compounds

| No. | Binding % | No. | Binding % | No. | Binding % | No. | Binding % |
|---|---|---|---|---|---|---|---|
| I-1 | + | I-2 | + | I-3 | + | I-4 | + |
| I-5 | +++ | I-6 | +++ | I-7 | ++ | I-8 | N/A |
| I-9 | +++ | I-10 | ++++ | I-11 | ++ | I-12 | +++ |
| I-13 | ++++ | I-14 | +++ | I-15 | +++ | I-16 | ++ |
| I-17 | ++++ | I-18 | +++ | I-19 | ++ | I-20 | +++ |
| II-1 | +++ | II-2 | +++ | II-3 | +++ | II-4 | ++ |
| II-5 | ++ | II-6 | +++ | II-7 | ++ | II-8 | +++ |
| II-9 | ++ | II-10 | +++ | II-11 | ++++ | II-12 | +++ |
| II-13 | +++ | N/A | N/A | N/A | N/A | N/A | N/A |

+ indicates binding activity from 0.5% to 5%
++ indicates binding activity from greater than 5% to 10%
+++ indicates binding activity from greater than 10% to 15%
++++ indicates binding activity from greater than 15%

All of the U.S. patents, U.S. patent application publications, U.S. patent applications, PCT published patent applications, foreign patents, foreign patent applications and non-patent publications referred to in this specification are incorporated herein by reference in their entirety.

U.S. non-provisional patent application Ser. Nos. 61/852,285 filed Mar. 15, 2013 and 61/889,328 filed on Oct. 10, 2013 are incorporated herein by reference, in their entirety.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

The invention claimed is:

1. A compound of Formula I:

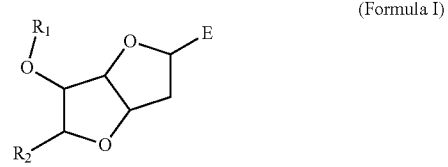

(Formula I)

or a stereoisomer thereof, or a pharmaceutically acceptable salt thereof, wherein:

R$_1$ is alkyl, heteroalkyl, cycloalkyl, cycloheteroalkyl, aryl, or heteroaryl, each of which is either unsubstituted or substituted with one or more R$_3$ groups;

R$_2$ is hydrogen, halogen, alkoxy, alkyl, heteroalkyl, cycloalkyl, cycloheteroalkyl, aryl or heteroaryl, wherein each of the alkoxy, alkyl, heteroalkyl, cycloalkyl, cycloheteroalkyl, aryl or heteroaryl is either unsubstituted or substituted with one or more $R_4$ groups;

$R_3$ is hydrogen, halogen, $OR_5$, $NR_6R_7$, cyano, oxo, alkyl, heteroalkyl, cycloalkyl, cycloheteroalkyl, aryl or heteroaryl, wherein each of the $OR_5$, $NR_6R_7$, alkyl, heteroalkyl, cycloalkyl, cycloheteroalkyl, aryl or heteroaryl is either unsubstituted or substituted with one or more $R_8$ groups;

$R_5$, $R_6$ and $R_7$ are independently hydrogen, alkyl, heteroalkyl, cycloalkyl, cycloheteroalkyl, aryl or heteroaryl, wherein each of the alkyl, heteroalkyl, cycloalkyl, cycloheteroalkyl, aryl or heteroaryl is either unsubstituted or substituted with one or more $R_9$ groups;

$R_4$, $R_8$ and $R_9$ are independently hydrogen, cyano, halogen, hydroxy, alkyl, alkoxy, heteroalkyl, cycloalkyl, cycloheteroalkyl, aryl, or heteroaryl, wherein each of the alkyl, alkoxy, heteroalkyl, cycloalkyl, cycloheteroalkyl, aryl, or heteroaryl is either unsubstituted or substituted with one or more $R_{10}$ groups;

each $R_{10}$ is independently halogen, hydroxy, alkyl, heteroalkyl, cycloalkyl, cycloheteroalkyl, aryl, or heteroaryl; and E is an electrophile capable of forming a covalent bond with the cysteine residue at position 12 of a K-Ras, H-Ras or N-ras G12C mutant protein and having one of the following structures:

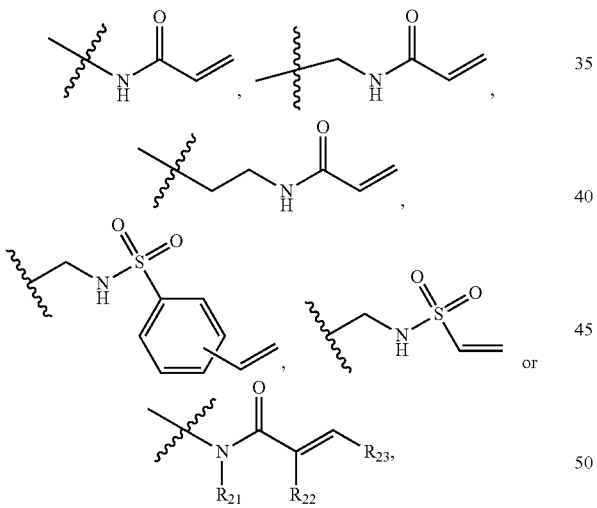

wherein:
$R_{21}$ is alkyl;
$R_{22}$ is CN or alkyl;
$R_{23}$ is alkyl;
or $R_{23}$ joins with $R_{22}$ to form a cycloalkene or aryl ring.

2. The compound of claim 1, wherein $R_2$ is —$CH_2$—$R_4$.
3. The compound of claim 2, wherein $R_4$ is OH.
4. The compound of claim 1, wherein $R_2$ is —O—$CH_2$—.
5. The compound of claim 4, wherein $R_4$ is $C_6H_5$.
6. The compound of claim 1, wherein $R_1$ is an alkyl, unsubstituted or substituted with one or more $R_3$ groups.
7. The compound of claim 1, wherein $R_1$ is an alkyl substituted with one or more $R_3$ groups, and wherein $R_3$ is aryl.

8. The compound of claim 1, wherein $R_1$ is —$CH_2$—$C_6H_5$.

9. The compound of claim 1, wherein E is

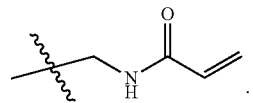 [SMILES: *CNC(=O)C=C]

10. The compound of claim 1, wherein the compound has one of the following structures:

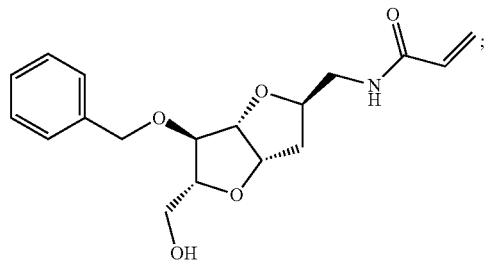

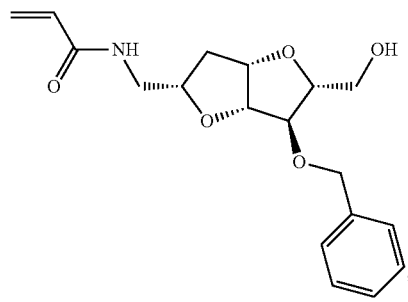

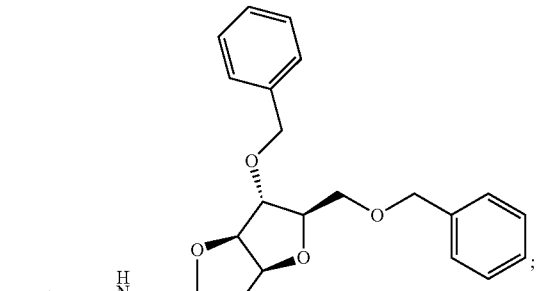

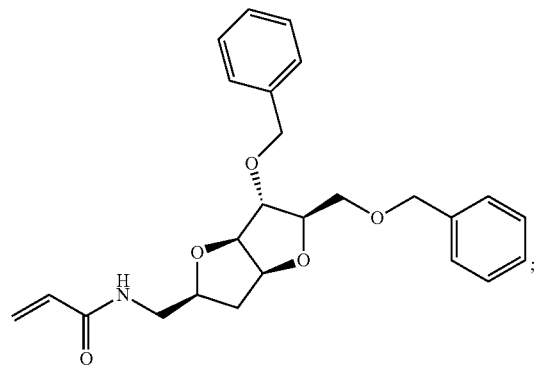

63
-continued
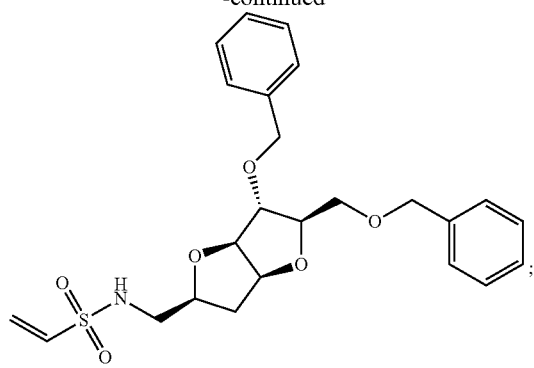
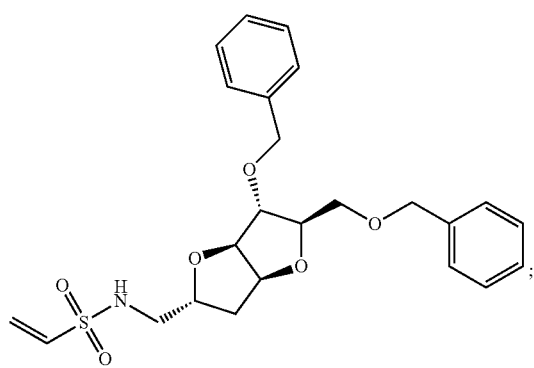
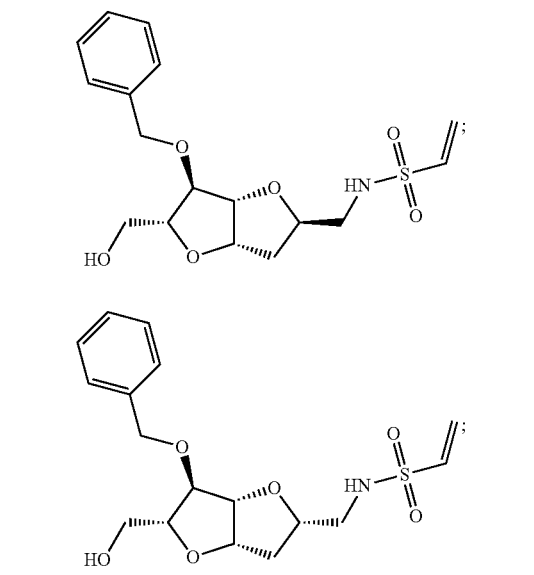
64
-continued
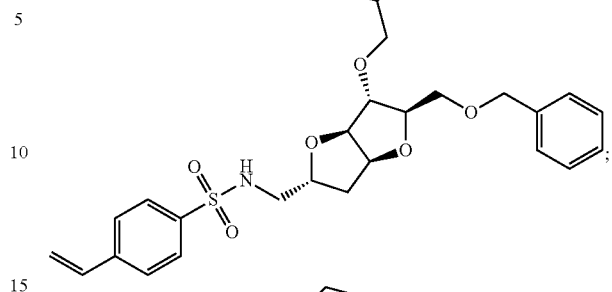
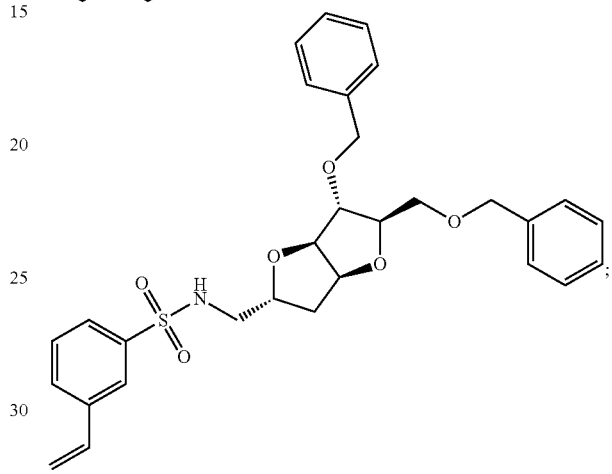
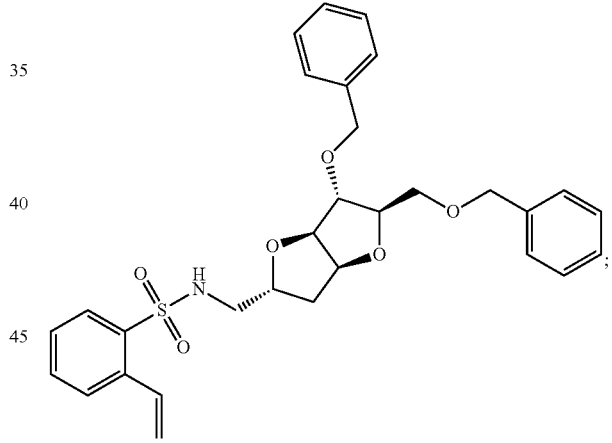
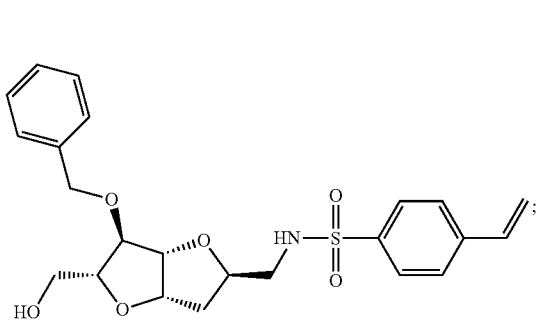
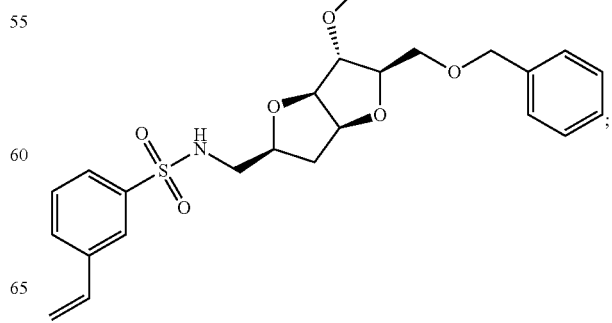

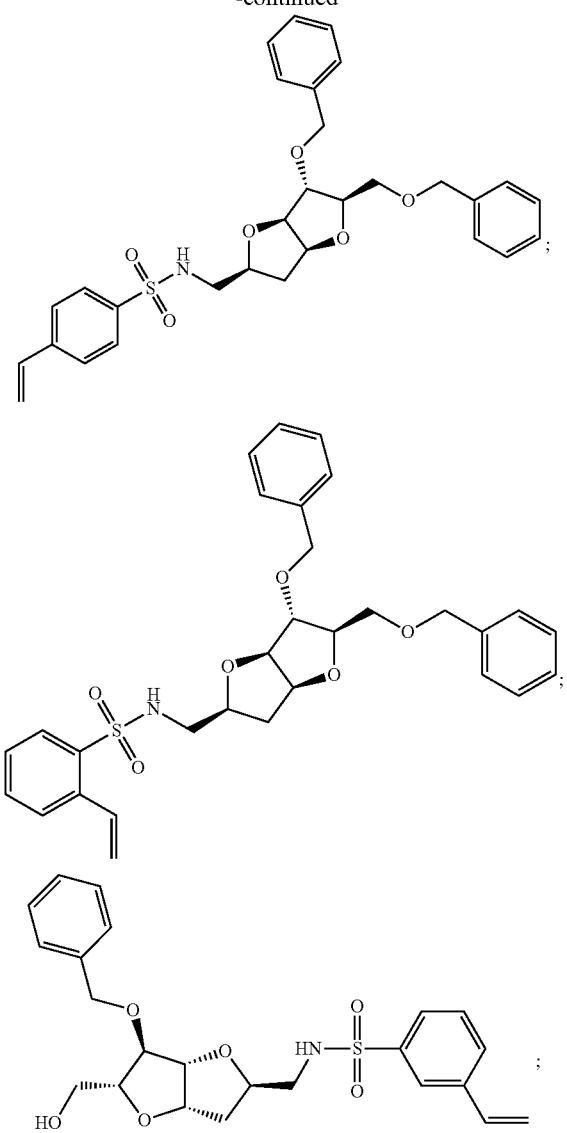
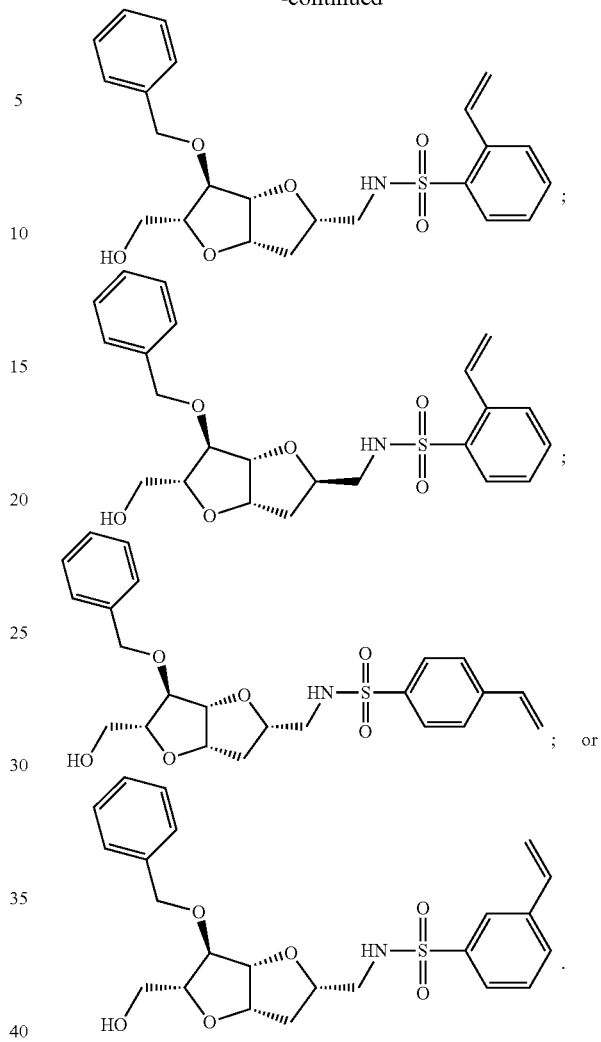
11. A pharmaceutical composition comprising a compound of claim 1 and a pharmaceutically acceptable carrier.
* * * * *